(12) United States Patent
Cousins et al.

(10) Patent No.: US 6,271,399 B1
(45) Date of Patent: Aug. 7, 2001

(54) ENDOTHELIN RECEPTOR ANTAGONISTS

(75) Inventors: Russell Donovan Cousins, Oxford; John Duncan Elliott, Wayne; Maria Amparo Lago, Audubon; Jack Dale Leber, Doylestown; Catherine Elizabeth Peishoff, West Chester, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/459,985

(22) Filed: Jun. 2, 1995

Related U.S. Application Data

(63) Continuation of application No. 08/336,444, filed on Nov. 9, 1994, now Pat. No. 5,817,693, which is a continuation-in-part of application No. PCT/US94/04603, filed on Apr. 26, 1994, which is a continuation-in-part of application No. 08/066,818, filed on Apr. 27, 1993, now abandoned, which is a continuation-in-part of application No. PCT/US92/09427, filed on Oct. 29, 1992, which is a continuation-in-part of application No. 07/854,195, filed on Mar. 20, 1992, now abandoned, which is a continuation-in-part of application No. 07/787,870, filed on Nov. 5, 1991, now abandoned.

(51) Int. Cl.$^7$ .................. C07D 317/54; C07D 319/14
(52) U.S. Cl. .................. 549/447; 549/362; 549/427; 549/436; 549/438; 549/439; 549/441; 549/444
(58) Field of Search .................. 549/436, 362, 549/447, 438, 439, 441, 444, 427

(56) References Cited

U.S. PATENT DOCUMENTS

| | | | |
|---|---|---|---|
| 5,716,984 | * 2/1998 | Cousins et al. | 514/464 |
| 5,716,985 | * 2/1998 | Elliott et al. | 514/464 |
| 5,718,183 | * 2/1998 | Cousins et al. | 514/464 |
| 5,817,693 | * 10/1998 | Cousins et al. | 514/464 |

* cited by examiner

*Primary Examiner*—Floyd D. Higel
(74) *Attorney, Agent, or Firm*—Linda E. Hall; Stephen A. Venetianer; Charles M. Kinzig

(57) ABSTRACT

Indane and indene compounds are described which are endothelin receptor antagonists.

7 Claims, No Drawings

ENDOTHELIN RECEPTOR ANTAGONISTS

This is a continuation of application Ser. No. 08/336,444, filed Nov. 9, 1994, now U.S. Pat. No. 5,817,693, which is a continuation-in-part of PCT/US94/04603 filed on Apr. 26, 1994, which is a continuation-in-part of Ser. No. 08/066,818 filed on Apr. 27, 1993, now abandoned, which is a continuation-in-part of PCT/US92/09427 filed on Oct. 29, 1992, which is a continuation-in-part of Ser. No. 07/854,195 filed on Mar. 20, 1992, now abandoned, which is a continuation-in-part of Ser. No. 07/787,870 filed on Nov. 5, 1991, now abandoned.

FIELD OF INVENTION

The present invention relates to novel indane and indene derivatives, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. *Br. J. Pharm.* 99:597–601, 1989 and Clozel and Clozel, *Circ. Res.*, 65:1193–1200, 1989) coronary vasospasm (Fukuda et al., *Eur. J. Pharm.* 165:301–304, 1989 and Lüscher, *Circ,* 83:701, 1991) heart failure, proliferation of vascular smooth muscle cells, (Takagi, *Biochem & Biophys. Res. Commun.;* 168:537–543, 1990, Bobek et al., *Am. J. Physiol.* 258:408–C415, 1990) and atherosclerosis, (Nakaki et al., *Biochem. & Biophys. Res. Commun.* 158:880–881, 1989, and Lerman et al., *New Eng. J. of Med.* 325:997–1001, 1991). Increased levels of endothelin have been shown after coronary balloon angioplasty (Kadel et al., No. 2491 *Circ.* 82:627, 1990).

Further, endothelin has been found to be a potent constrictor of isolated mammalian airway tissue including human bronchus (Uchida et al., *Eur. J. of Pharm.* 154:227–228 1988, LaGente, *Clin. Exp. Allergy* 20:343–348, 1990; and Springall et al., *Lancet,* 337:697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., *Br. J. Pharm.* 95:1011–1013, 1988); Raynaud's phenomenon, Cinniniello et al., *Lancet* 337:114–115, 1991); Crohn's Disease and ulcerative colitis, Munch et al, *Lancet,* Vol. 339, p. 381; Migraine (Edmeads, Headache, February 1991 p 127); Sepsis (Weitzberg et al., *Circ. Shock* 33:222–227, 1991; Pittet et al., *Ann. Surg.* 213:262–264, 1991), Cyclosporin-induced renal failure or hypertension (*Eur. J. Pharmacol.,* 180:191–192, 1990, *Kidney Int,* 37:1487–1491, 1990) and endotoxin shock and other endotoxin induced diseases (*Biochem. Biophys. Res. Commun.,* 161:1220–1227, 1989, *Acta Physiol. Scand.* 137:317–318, 1989) and inflammatory skin diseases, (*Clin Res.* 41:451 and 484, 1993) and macular degeneration.

Endothelin has also been implicated in preclampsia of pregnancy. Clark et al.,*Am. J. Obstet. Gynecol,* March 1992, p. 962–968; Kamor et al., *N. Eng. J. of Med.,* Nov. 22, 1990, p. 1486–1487; Dekker et al., *Eur J. Ob. and Gyn. and Rep. Bio.* 40 (1991) 215–220; Schiff et al., *Am. J. Obstet. Gynecol.* February 1992, p. 624–628; diabetes mellitus, Takahashi et al.,*Diabetologia* (1990) 33:306–310; and acute vascular rejection following kidney transplant, Watschinger et al., *Transplantation* Vol. 52, No. 4, pp. 743–746.

Endothelin stimulates both bone resorption and anabolism and may have a role in the coupling of bone remodeling. Tatrai et al *Endocrinology,* Vol. 131, p. 603–607.

Endothelin has been reported to stimulate the transport of sperm in the uterine cavity, Casey et al., *J. Clin. Endo and Metabolism,* Vol. 74, No. 1, p. 223–225, therefore endothelin antagonists may be useful as male contraceptives. Endothelin modulates the ovarian/menstrual cycle, Kenegsberg, *J. of Clin. Endo. and Met.,* Vol. 74, No. 1, p. 12, and may also play a role in the regulation of penile vascular tone in man, Lau et al., *Asia Pacific J. of Pharm.,* 1991, 6:287–292 and Tejada et al., *J. Amer. Physio. Soc.* 1991, H1078–H1085. Endothelin also mediates a potent contraction of human prostatic smooth muscle, Langenstroer et al., *J. Urology,* Vol. 149, p. 495–499.

Thus, endothelin receptor antagonists would offer a unique approach toward the pharmacotherapy of hypertension, renal failure, ischemia induced renal failure, sepsis-endotoxin induced renal failure, prophylaxis and/or treatment of radio-contrast induced renal failure, acute and chronic cyclosporin induced renal failure, cerebrovascular disease, myocardial ischemia, angina, congestive heart failure, asthma, atherosclerosis, macular degeneration, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention or treatment of restenosis, diabetes, preclampsia of pregnancy, bone remodeling, kidney transplant, male contraceptives, infertility and priaprism and benign prostatic hypertrophy.

SUMMARY OF THE INVENTION

This invention comprises indane and indene derivatives represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure, atherosclerosis, and as an adjunct in angioplasty for prevention of restenosis and benign prostatic hypertrophy.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

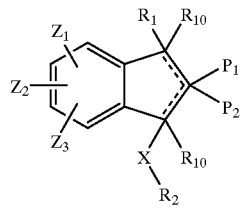

(I)

wherein:
$R_1$ is —$X(CH_2)_n Ar$ or —$X(CH_2)_n R_8$ or

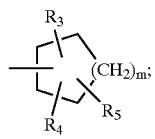

(c)

$R_2$ is hydrogen, Ar, $C_{1-4}$alkyl or (c);
$P_1$ is —$X(CH_2)_n R_8$;
$P_2$ is —$X(CH_2)_n R_8$, or —$X—R_9—Y$;
$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, $NHCOR_6$, $R_{13}CO_2R_7$, —$X—R_9—Y$, or —$X(CH_2)_n R_8$ wherein each methylene group within —$X(CH_2)_n R_8$ may be unsubstituted or substituted by one or two —$(CH_2)_n Ar$ groups;
$R_4$ is hydrogen, $R_{11}$, OH, $C_{1-5}$alkoxy, $S(O)_q R_{11}$, $N(R_6)_2$, Br, F, I, Cl or $NHCOR_6$ wherein the $C_{1-5}$alkoxy may be unsubstituted or substituted by OH, methoxy or halogen;
$R_6$ is independently hydrogen or $C_{1-4}$alkyl;
$R_7$ is independently hydrogen, $C_{1-10}$alkyl, $C_{2-10}$alkenyl or $C_{2-8}$ alkynyl, all of which may be unsubstituted or substituted by one or more OH, N(R6)2, CO2R12, halogen or XC1-5alkyl; or R7 is (CH2)nAr;

$R_8$ is hydrogen, R11, CO2R7, CO2C(R11)2 O(CO)XR7, PO3(R7)2, $SO_2 NR_7 R_{11}$, $NR_7 SO_2 R_{11}$, $CONR_7 SO_2 R_{11}$, $SO_3 R_7$, $SO_2 R_7$, $P(O)(OR_7)R_7$, CN, —$CO_2(CH_2)_m C(O)N(R_6)_2$, $C(R_{11})_2 N(R_7)_2$, $C(O)N(R_6)_2$, tetrazole or $OR_6$;
$R_9$ is a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R_6)_2$, COOH or halogen;
$R_{10}$ is $R_3$ or $R_4$;
$R_{11}$ is hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;
$R_{12}$ is hydrogen, $C_{1-6}$alkyl, $C_{2-6}$alkenyl or $C_{2-7}$alkynyl;
$R_{13}$ is divalent Ar, $C_{1-10}$alkylene, $C_{1-10}$alkylidene, $C_{2-10}$alkenylene, $C_{2-10}$ alkynylene, all of which may be unsubstituted or substituted by one or more OH, $CH_2OH$, $NR_6)_2$ or halogen;
X is $(CH_2)_n$, O, $NR_6$ or $S(O)_q$;
Y is $CH_3$ or $X(CH_2)_n Ar$;
Ar is:

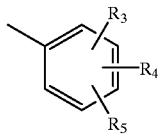

(a)

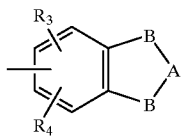

(b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;
A is C=O or $(C(R_6)_2)_m$;
B is —$CH_2$— or —O—;
$Z_1$ and $Z_2$ are independently hydrogen, $C_{1-8}$alkyl, $C_{2-8}$alkenyl, $C_{2-8}$alkynyl, OH, $C_{1-8}$alkoxy, $S(O)_q C_{1-8}$alkyl, $NR_6)_2$, Br, F, I, Cl, $NHCOR_6$, —$X—R_9—Y$, —$X(CH_2)_n R_8$, phenyl, benzyl or $C_{3-6}$cycloalkyl wherein the $C_{1-8}$alkyl, $C_{2-8}$alkenyl or $C_{2-8}$alkynyl may be optionally substituted by COOH, OH, $CO(CH_2)_n CH_3$, $CO(CH_2)_n CH_2 N(R_6)_2$, or halogen; or $Z_1$ and $Z_2$ together may be -O-A-O on contiguous carbons;
$Z_3$ is $Z_1$ or —$X—R_9—Y$;
q is zero, one or two;
n is an integer from 0 to six;
m is 1, 2 or 3;and the dotted line indicates the optional presence of a double bond; or a pharmaceutically acceptable salt thereof; provided that
$R_2$ is not hydrogen when X is $S(O)_q$;
when the optional double bond is present there is only one $R_{10}$ and there is no $P_1$ and $P_2$ is not $NR_6 R_9 Y$; and if X—$R_2$ is attached to the double bond, X is not $NR_6$; and if $R_1$ is attached directly to the double bond, $R_1$ is not $NR_6 Ar$;
when $R_3$, $R_5$, $Z_1$, $Z_2$, or $Z_3$ is $X(CH_2)_n R_8$ and n is not 0, X is oxygen or $NR_6$ when $R_8$ is $OR_6$ or $CO_2 H$;
when $R_8$ is $CO_2 C(R_{11})_2 O(CO)XR_7$, X is not $S(O)_q$;
the compound of Formula I is not (1RS)-1,3-diphenylindene-2-carboxylic acid; (cis,cis)-(1RS,3SR)-1,3- diphenylindane-2-carboxylic acid; (1RS)-3-[3-Methyl-1-phenyl-(1H)-ind-2-en-1-yl] propionic acid; or (1RS)-2[1,3-diphenyl-(1H)-ind-2-en-2-yl]ethanoic acid; 1,3-diphenyl-1-ethoxyindene-2-carboxylic acid; 1,2,3-triphenylindene; 1,3-diphenylindene; 1-(2,3-dimethyl-2-buten-yl)-1,3-diphenylindene; 1,3-diphenyl-2-methylindene; 1,3-diphenyl-2-methylindane; 1,3-diphenylindane; 5,6-dimethoxy-1,3-dimethoxyindene; 1,3-bis(4,5-dimethoxy-2-hydroxyphenyl)-5,6-dimethoxyindane; 1,3-bis(3,4-dimethoxyphenyl)-5,6-dimethoxyindane; 1,3-diphenyl-2-methoxyidene, 1,3-diphenyl-2-ethoxyindene, 5-fluoro-2-methyl-indene-3-acetic acid, methyl 1,3-diphenylindene-2-carboxylate, ethyl 1,3-diphenylindene-2carboxylate, or 2-cyano-1,3-diphenylindene.

Also included in the invention are pharmaceutically acceptable salt complexes. Preferred are the ethylene diamine, sodium, potassium, calcium and ethanolamine salts.

The term alkylene is a divalent alkyl group in which the bonds are on two different carbon atoms; alkylidene is a divalent alkyl group in which the bonds are on the same carbon atom; alkenylene is a divalent alkene group in which the bonds may be on any carbon atom; alkynylene is a divalent alkynyl group in which the bonds may be on any carbon atom.

All alkyl, alkenyl, alkynyl, alkoxy, alkylene, alkylidene, alkenylene and alkynylene groups may be straight or branched. The term "halogen" is used to mean iodo, fluoro, chloro or bromo. Alkyl groups may be substituted by one or more halogens up to perhalogenation.

The compounds of the present invention may contain one or more asymmetric carbon atoms and may exist in racemic and optically active form. All of these compounds and diastereoisomers are contemplated to be within the scope of the present invention.

Preferred compounds are those wherein $R_1$ is $X(CH_2)_nAr$, (Ar is (a) or (b)), dihydrobenzofuranyl, benzodioxanyl, cyclohexyl or $C_{1-4}$alkyl; $R_2$ is a moiety of formula (a) or (b), $C_{1-4}$alkyl, indolyl or hydrogen; $R_3$ and $R_5$ are independently hydrogen, OH, $C_{1-5}$alkoxy, halogen, —$OC_{1-4}$alkyl phenyl, $R_{13}CO_2R_7$, $C_{1-4}$alkyl, $N(R_6)_2$, NH(CO)CH$_3$, —X(CH$_2$)$_n$R$_8$, —X—R$_9$—Y pyridyl, phenyl or $S(O)_qC_{1-5}$ alkyl; $R_4$ is hydrogen, OH, $C_{1-5}$alkoxy, halogen, $C_{1-4}$alkyl, $N(R_6)_2$, NH(CO)CH$_3$ or $S(O)_qC_{1-5}$alkyl; $Z_1$, $Z_2$ and $Z_3$ are independently $XR_9Y$, benzyl, hydrogen, OH, $C_{1-5}$alkoxy, —$N(R_6)_2$, $S(O)_qC_{1-8}$alkyl, NHCOR$_6$, $X(CH_2)_nR_8$ or halogen, or $Z_1$ and $Z_2$ together may be -O-A-O on contiguous carbons; $P_1$ and $P_2$ are independently hydrogen, CO$_2$H, $C(R_6)_2CO_2H$ or tetrazole; Ar is a moiety of formula (a) or (b), phenyl, or pyridyl; X is (CH$_2$)$_n$ or oxygen.

More preferred are compounds wherein $R_3$ is hydrogen, —X(CH$_2$)$_n$R$_8$ or $R_{13}CO_2R_7$; $R_4$ and $R_5$ are independently hydrogen, OH, $C_{1-5}$alkoxy, $SC_{1-5}$alkyl, substituted phenyl, F, Br, $C_{1-3}$alkyl or NH$_2$; $Z_1$ and $Z_3$ are hydrogen and $Z_2$ is hydrogen, OH, $C_{1-5}$alkoxy, halogen, $X(CH_2)_nR_8$, NH$_2$, benzyl, NH(CO)CH$_3$, or $Z_1$ and $Z_2$ together may be O-A-O on contiguous carbons and $R_1$, $R_2$, $P_1$, $P_2$, Ar and X are as above for preferred compounds.

Most preferred are compounds wherein $R_1$ is (b) and $R_2$ is (a) or (b); A is CH$_2$, B is —O—; there is no optional double bond; $R_1$ and XR$_2$ are trans to $P_1$; $Z_2$ is hydrogen, OH, $C_{1-5}$alkoxy, or —OCH$_2$CH=CH$_2$, $Z_1$ is hydrogen; $R_3$ is XAr, hydrogen, $X(CH_2)_n$ COOH, $X(CH_2)_n$ CONR$_7$SO$_2$R$_{11}$, $X[(CR_6)_2]_nOR_6$ or CH=CHCO$_2$H; $R_4$ is hydrogen, substituted phenyl, pyridyl or pyrimidyl, or $C_{1-2}$alkoxy; $R_5$, $R_{10}$ and $P_2$ are hydrogen, and $P_1$ is CO$_2$H or $C(R_6)_2CO_2H$.

Especially preferred are compounds wherein $R_1$ is (b) and $R_2$ is (a); A is CH$_2$, B is —O—; there is no optional double bond; $R_1$ and XR$_2$ are trans to $P_1$; X is a bond; $Z_1$ and $Z_3$ are hydrogen; $Z_2$ is hydrogen, OH or $C_{1-5}$alkoxy; $R_3$ is hydrogen, OAr (where Ar is (a), (b), pyridyl or pyrimidyl and A is CH$_2$ and B is —O— and Ar may be substituted by CO$_2$H), O(CH$_2$)$_{1-3}$CO$_2$H, O(CH$_2$)$_{1-3}$CONHSO$_2$R$_{11}$, (CH$_2$)$_{0-4}$CO$_2$H, (CH$_2$)$_{0-3}$CONH SO$_2$ R$_{11}$, or O[(CR$_6$)$_2$]$_{2-4}$OH; $R_4$ is hydrogen, $C_{1-2}$alkoxy, or phenyl, pyridyl or pyrimidyl all of which may be substituted by $R_3$ or $C_{1-2}$alkoxy; $R_5$, $R_{10}$ and $P_2$ are hydrogen; and $P_1$ is CO$_2$H or CH$_2$CO$_2$H.

Especially preferred compounds are the following:

(1RS,2SR,3RS)-3-(2-Carboxymethoxy-4-methoxyphenyl)-1-(3,4-methylenedioxyphenyl)-5-(prop-1-yloxy)indane-2-carboxylic acid;

(+)(1S,2R,3S)-3-(2-Carboxymethoxy-4-methoxyphenyl)-1-(3,4-methylenedioxyphenyl)-5-(prop-1-yloxy)-indane-2-carboxylic acid;

(+)(1S,2R,3S)-3-(2-Carboxymethoxy-4-methoxyphenyl)-1-(3,4-methylenedioxyphenyl)-5-(prop-1-yloxy)-indane-2-carboxylic acid disodium salt;

(1RS,2SR,3SR)-3-(2-Carboxymethoxy-4-methoxyphenyl)-1-(2-methoxy-4,5-methylenedioxyphenyl)-5-(prop-1-yloxy)indane-2-carboxylic acid;

(1RS,2SR,3RS)-3-[2-(2-Carboxyeth-1-yloxy]-4-methoxyphenyl]-1-(3,4-methylenedioxyphenyl)-5-(prop-1-yloxy)indane-2-carboxylic acid;

(1RS, 2SR,3SR)-3-[2-[(E)-2-Carboxyethen-1-yl]-4-methoxyphenyl]-1-(3,4-methylenedioxybenyl)-5-(prop-1-yloxy)indane-2-carboxylic acid;

(1RS,2SR,3SR)-3-[2-(2-Carboxyeth-1-yl)4-methoxyphenyl]-1-(3,4-methylenedioxyphenyl)-5-(prop- 1-yloxy)-indane-2-carboxylic acid;

(1RS,2SR,3RS)-3-[2-(3-Carboxyphenyl)-4-methoxyphenyl]-1-(3,4-methylenedioxyphenyl)-5-(prop-1-yloxy)indane-2-carboxylic acid;

(+)(1S,2R,3S)-3-[2-[(4Carboxypyridin-3-yloxy]-4-methoxyphenyl]-1-(3,4-methylenedioxyphenyl)-5-(prop-1-yloxy)indane-2-carboxylic acid;

(+)(1S,2R,3S)-3-[2-(2-Hydroxyeth-1-yloxy)-4-methoxyphenyl]-1-(3,4-methylenedioxyphenyl)-5-(prop-1-yloxy)indane-2-carboxylic acid;

(1RS,2SR,3RS)-3-[2-(2-Hydroxyeth-1-yloxy) methoxyphenyl]-1-(3,4-methylenedioxyphenyl)-5-(prop-1-yloxy)indane-2-carboxylic acid;

(+)(1S,2R,3S)-3-[2-(2-Hydroxyeth-1-yloxy)-4methoxyphenyl]-1-(3,4-methylenedioxyphenyl)-5-(prop 1-yloxy)indane-2-carboxylic acid hemiethylenediamine salt;

(1RS,2SR,3RS)-3-(2-carboxymethoxy-4-methoxyphenyl)-1-(3,4-methylenedioxyphenyl)-5-(prop-1-yloxy)indane-2-yl-acetic acid.

(1RS,2SR,3RS)-3-[2-(2-Hydroxyeth-1-yloxy)4-methoxyphenyl]-1-(3,4-methylenedioxyphenyl)-5-(prop-1-yloxy)indan-2-yl acetic acid The present invention provides compounds of Formula (I) above

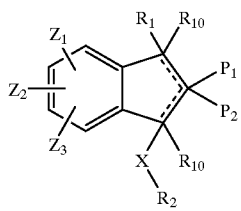
(I)

which can be prepared by a process which comprises:

a) reacting a compound of Formula (2) wherein X is $C_{1-5}$alkyl

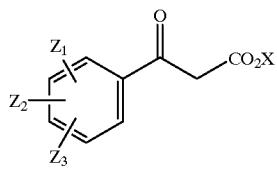
(2)

with a substituted benzaldehyde or aldehyde of Formula (3).

D-CHO (3)

wherein D is Ar or (c) as defined in Formula I, in a suitable solvent such as benzene with a catalyst such as piperidinium acetate at reflux to provide a compound of Formula (4).

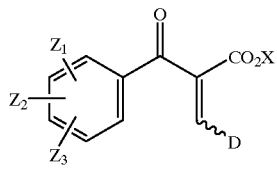
(4)

Cyclization of compound (4) in the presence of a suitable Lewis acid such as titanium tetracholoride or aluminum chloride or alternatively when $Z_1$ is 3-OR (meta)(where R is $C_{1-5}$alkyl, or benzyl), trifluoroacetic acid, provides an indanone of the Formula (5).

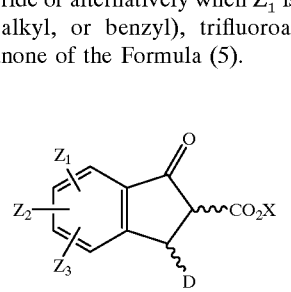
(5)

Dehydrogenation with 2,3-dichloro-5,6-dicyano-1,4-benzoquinone in an appropriate solvent or alternatively bromination with pyridinium hydrobromide perbromide in dichloromethane followed by treatment with 1,5-diazabicyclo[4,3,0]non-5-ene provides indenones of Formula (6).

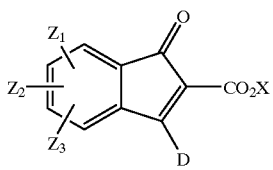
(6)

b) Alternatively, a compound of Formula 6 wherein $Z_1$, $Z_2$ and $Z_3$ are hydrogen and

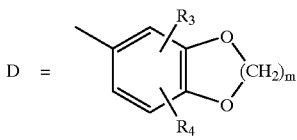

can be prepared by treatment of 2-bromobenzoic acid with two equivalents of n-butyllithium in a solvent such as tetrahydrofuran under argon at −78° C. followed by the addition of an acid chloride of Formula (7):

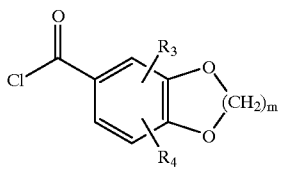
(7)

provides a compound of Formula (8):

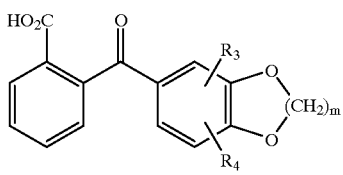
(8)

Treatment of compounds of type (8) with thionyl chloride at reflux gives an acid chloride which can be isolated by concentration under reduced pressure. This acid chloride can then be treated with diethyl magnesium malonate in a solvent such as ether to give a compound of Formula (9):

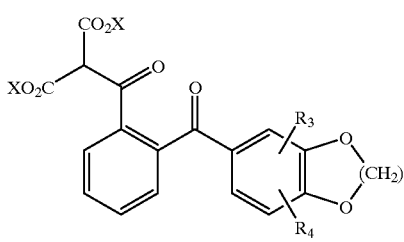
(9)

Reaction of a compound of type (9) at reflux with 5% aqueous sodium carbonate gives compounds of Formula (10):

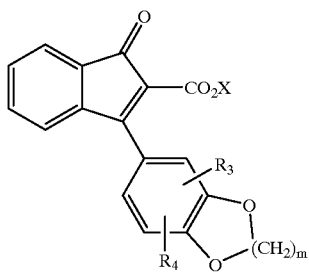

(10)

c) Treatment of an indenone of Formula (11):

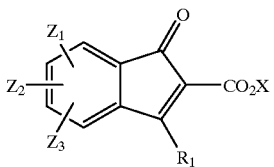

(11)

wherein $Z_1$, $Z_2$, $Z_3$ and $R_1$ are as defined for formula I or a group convertable to them, with an organomagnesium compound of Formula (12) wherein $R_2$ is defined for $$R_2(CH_2)_n MgBr \quad (12)$$

Formula I or a group convertable to it, in a suitable solvent provides compounds of Formula (13):

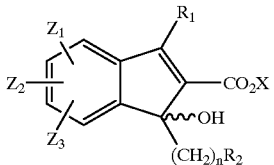

(13)

Saponification of compounds of Formula (13) using sodium hydroxide in aqueous methanol followed by reduction with triethylsilane and boron trifluoride etherate in a suitable solvent such as dichloromethane at 0° C. affords racemic compounds of Formula (14)

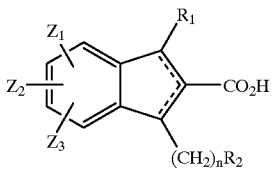

(14)

Conjugate addition of nucleophiles to an ester derived from Formula (14), followed by saponification affords compounds of Formula (1) having an $R_{10}$ other than hydrogen. Re-introduction of a double bond into an ester derived from such acids followed by conjugate addition of another nucleophilic species and subsequent saponification affords compounds of Formula (1) in which neither $R_{10}$ substituent is hydrogen.

Reduction of compounds of Formula (13) with triethylsilane and boron trifluoride etherate in a suitable solvent such as dichloromethane at 0° C. followed by hydrogenation with hydrogen gas under pressure at approximately 60 psi in the presence of a suitable catalyst such as 10% palladium on charcoal affords compounds of Formula (15):

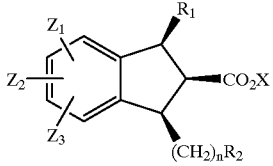

(15)

Alkylation or acylation of the ester enolate derived from Formula (15) affords compounds wherein $P_1$ and $P_2$ are as defined in Formula (I).

Alternatively, hydrogenation of compounds of Formula (13) with hydrogen gas under pressure at approximately 60 psi in the presence of a suitable catalyst such as 10% palladium on charcoal in a suitable solvent such as ethyl acetate or methanol containing 1–5% acetic acid affords compounds of Formula (15). Treatment of these compounds with a base such as sodium hydroxide in a suitable solvent such as aqueous ethanol provides racemic compounds of Formula (16):

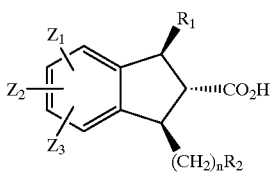

(16)

wherein $Z_1$, $Z_2$ and $Z_3$ are hydrogen; $R_1=R_2$; and n is 0. Treatment of compounds of Formula (13) with triethylsilane and boron trifluoride etherate in a suitable solvent such as dichloromethane at 0° C. followed by reaction with samarium II iodide in a suitable solvent such as tetrahydrofuran and then saponification, provides compounds of Formula (17)

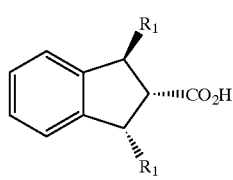

(17)

With appropriate manipulation and protection of any chemical functionalities, synthesis of the remaining compounds of the Formula (I) is accomplished by methods analogous to those above and to those described in the Experimental section In order to use a compound of the Formula (I) or a pharmaceutically acceptable salt thereof for the treatment of humans and other mammals it is normally formulated in accordance with standard pharmaceutical practice as a pharmaceutical composition Compounds of Formula (1) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from I to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation (Rat cerebellum or kidney cortex)

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000×g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 micrograms of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 micrograms of membrane protein was used for each tube in binding experiments.

B) CHO Cell Membrane on

CHO cells stably transfected with human $ET_A$ and $ET_B$ receptors were grown in 245 mm×245 mm tissue culture plates in Dulbecco's modified Eagle's medium (DMEM) supplemented with 10% fetal bovine serum (FBS). The confluent cells were washed with DPBS (Dulbecco's phosphate buffered saline) containing protease inhibitor cockatil (5 mM EDTA, 0.5 mM PMSF, 5 ug/ml leupeptin, and 0.1 U/ml aprotinin) and scraped in the same buffer. After centrifugation at 800×g, the cells were lysed by freezing in liquid nitrogen and thawing on ice followed by homogenization (30 times using glass dounce homogenizer) in lysis buffer containing 20 mM Tris HCl, pH 7.5 and the protease inhibitor cocktail. After an initital centrifugation at 800×g for 10 min to remove unbroken cells and nuclei, the supernatants were centrifuged at 40,000×g for 15 min and the pellet was resuspended in 50 mM Tris HCl, pH 7.5 and 10 mM $MgCl_2$ and stored in small aliquots at −70° C. after freezing in liquid $N_2$. Protein was determined using BCA method and bovine serum albumin as the standard.

C) [$^{125}$I]ET-1 Binding Protocol

[$^{125}$I]ET-1 binding to membranes from rat cerebellum (2–5 mg protein/assay tube) or kidney cortex (3–8 micrograms protein/assay tube) or CHO cell membranes (containing 4–6 and 1–2 micrograms of membrane protein for $ET_A$ and $ET_B$ receptors, respectively) were measured after 60 minutes incubation at 30° C. in 50 mM Tris HCl, 10 mM $MgCl_2$, 0.05% BSA, pH 7.5 buffer in a total volume of 100 microliters. Membrane p rotein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM $MgCl_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. $IC_{50}$'s for the compounds of this invention range from 0.01 nm to 50 uM.

II. In Vitro Vascular Smooth Muscle Activity

Rat aorta are cleaned of connective tissue and adherent fat, and Cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; $KH_2PO_4$, 1.2; $MgSO_4$, 1.2; $CaCl_2$, 2.5; $NaHCO_3$, 25.0; and dextrose, 11.0. Tissue bath solutions are maintained at 37° C. and aerated continuously with 95% $O_2$/5% $CO_2$. Resting tensions of aorta are maintained at I g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ±S.E.M. Dissociation constants ($K_b$) of competitive antagonists were determined by the standard method of Arunlakshana and Schild. The potency range for compounds of this invention range from 0.01 nM to 50 uM.

The following examples are illustrative and are not limiting of the compounds of this invention.

EXAMPLE 1

(1RS,2RS,3SR)-1-(4-Methoxypbenyl)-3-phenylindane-2-carboxylic acid a) Ethyl (1RS)[1-Hydroxy-1-(4methoxyphenyl)1-3-phenylindene-2-carboxylate. To dry magnesium turnings (0.88 g, 36 mmol) under an argon atmosphere was added, portionwise, a solution of p-bromoanisole (4.5 ml, 36 mmol) in 5% $THF/Et_2O$ (37 ml). The resulting p-methoxyphenyl magnesium bromide solution was added to a solution of ethyl 1-oxo-3-phenylindene-2-carboxylate (5.0 g, 18 mmol) in $Et_2O$ (300 ml) under an argon atmosphere at 0° C. The resulting mixture was allowed to warm to room temperature and was stirred for 10 min. The mixture was partitioned between 3M HCl (100 ml) and EtOAc (200 ml). The organic extract was washed successively with $H_2O$, aqueous $NaHCO_3$, $H_2O$ and saturated aqueous NaCl and dried ($Na_2SO_4$). The solvent was removed in vacuo to provide a yellow oil which was treated with $Et_2O$/hexanes. The solid which formed was collected by filtration (3.47 g). The filtrate was concentrated under reduced pressure and purified by flash chromatography. The material which was isolated was treated with $Et_2O$/ hexanes, and the additional solid which formed (1.76 g, 75% total yield) was collected by filtration to afford the title compound.

b) Ethyl (RS)-1(4-Methoxyphenyl)-3-phenylindene-2-carboxylate. To a solution of ethyl (1RS) [1-hydroxy-1-(4methoxyphenyl)]-3-phenylindene-2-carboxylate (4.65 g, 12.0 mmol) in $CH_2Cl_2$ (40 ml) at 0° C. under an argon atmosphere was added triethylsilane (2.34 ml, 14.6 mmol), followed by boron trifluoride etherate (8.8 ml, 71 mmol). The reaction mixture was allowed to warm to room temperature and stirred for 10 min, at which time was added slowly 3M HCl (50 ml). The mixture was extracted with EtOAc (150 ml). The organic extract was washed successively with $H_2O$, aqueous $NaHCO_3$, $H_2O$ and saturated aqueous NaCl and dried. The solvent was removed in vacuo, and the residue was purified by flash chromatography on silica gel, eluting with 10% EtOAc/ hexanes to provide the title compound (4.2 g, 95%) as a mixture of Δ1 and Δ2 double bond isomers.

c) Ethyl (1RS,2SR,3SR)-1-(4Methoxyphenyl)-3-phenylindane-2-carboxylate. To a solution of ethyl (RS)-I-(4methoxyphenyl)-3-phenylindene-2-carboxylate (5.75 g, 15 mmol) in EtOAc (150 ml) was added 5% palladium on activated carbon (600 mg). The resulting suspension was stirred under an atmosphere of $H_2$ for 1 d, then was filtered through a pad of Celite. The filtrate was concentrated under reduced pressure to afford the title compound, which was used without further purification.

d) (1RS.2RS.3SR)-1-(4-Methoxyphenyl)-3-phenylindane-2-carboxylic acid. To a solution of ethyl (1RS, 2SR,3SR)-1-(4-methoxyphenyl)3-phenylindane-2-carboxylate, (5.5 g, 14.8 mmol) in EtOH (70 ml) was added 5M NaOH (9 ml, 45 mmol). The resulting mixture was stirred under an argon atmosphere for 1 d, at which time $H_2O$ (70 ml) was added. The mixture was concentrated under reduced pressure. The aqueous residue was extracted with $Et_2O$, and the $Et_2O$ extracts were discarded. The aqueous phase was acidified with 6M HCl and extracted several times with EtOAc. The combined EtOAc extracts were washed successively with $H_2O$ and saturated aqueous NaCl and dried. The solvent was removed in vacuo to provide an oily residue which crystallized upon standing. The solid material was recrystallized from EtOAc/ hexanes to afford the title compound (4.25 g, 83%); m.p. 164–166° C.

$^1$H NMR ($CDCl_3$): δ 7.35–7.18 (m, 9H); 6.92–6.88 (m, 4H); 4.68 (d, 1H, J=10 Hz); 4.64 (d, 1H, J=10 Hz); 3.81 (s, 3H); 3.34 (t, 1H, J=10 Hz).

MS: 345 [$(M+H)^+$].

Anal. Calc. for $C_{23}H_{20}O_3$: C, 80.21; H, 5.85.

Found C, 80.21; H 6.03.

EXAMPLE 2

(trans, trans)-1,3-Di(4-methoxyphenyl)-indane-2-carboxylic acid a) Ethyl 2-Benzoyl-3-(4-hydroxyphenyl)propenoate. To a solution of 4-hydroxybenzaldehyde (31.7 g, 0.26 mol) and ethyl benzoylacetate (45.5 ml, 0.26 mol) in EtOH (45 ml) under an argon atmosphere was added piperidine (2.6 ml, 0.026 mol) and acetic acid (3 drops). After stirring at room temperature overnight, the resulting solid mixture was treated with hot EtOH (700 ml), and then allowed to cool. The crystals which formed were collected by filtration to afford the title compound (61.0 g, 79%).

b) Ethyl (2RS ,3SR)-3-(4-Hydroxyphenyl)-1-oxoindane-2-carboxylate. To a mixture of ethyl 2-benzoyl-3-(4hydroxyphenyl)propenoate (0.50 g, 1.7 mmol) in $CH_2Cl_2$ (15 ml) at 0C under an argon atmosphere was added titanium tetrachloride (0.93 ml, 8.3 mmol). The resulting mixture was allowed to stir at room temperature overnight. The reaction was slowly quenched with 3M HCl, then partitioned between EtOAc (50 ml) and 3M HCl. The aqueous phase was extracted with EtOAc, and the combined organic extracts were washed successively with H₂O and saturated aqueous NaCl, and dried (Na₂SO₄). The solvent was removed in vacuo, and the solid residue was recrystallized from EtOAc/ hexanes to afford the title compound (410 mg, 82%).

c) Ethyl (2RS,3SR)-3-(4-t-Butyldimethylsiloxyphenyl)-1-oxoindane-2-carboxylate. To a solution of ethyl (2RS, 3SR)-3-(4-hydroxyphenyl)-1-oxoindane-2-carboxylate (3.0 g, 10.2 mmol) in DMF (10 ml) under an argon atmosphere were added imidazole (1.72 g, 25.3 mmol) and t-butyldimethylchloro-silane (1.82 g, 12.1 mmol). The resulting mixture was allowed to stir at room temperature for 3 d, then was poured into dilute aqueous HCl and extracted with EtOAc (2×). The combined organic extracts were washed successively with H₂O, aqueous NaHCO₃, H₂O and saturated aqueous NaCl and dried. The solvent was removed in vacuo to provide the title compound (5.40 g) which was used without further purification.

d) Ethyl 3-(4-t-Butyldimethylsiloxyphenyl)-1-oxoindene-2-carboxylate. To a solution of ethyl (2RS,3SR)-3-(4-t-butyldimethylsiloxyphenyl)-1-oxoindane-2-carboxylate (130 mg, 0.32 mmol) in CH₂Cl₂ (3 ml) under an argon atmosphere was added 2,3-dichloro-5,6-dicyano-1,4-benzoquinone (80 mg, 0.35 mmol). The resulting mixture was stirred for 2.5 h. Aqueous NaHSO₃ and EtOAc were added, and the mixture was stirred for 5 min. The aqueous phase was separated and extracted with EtOAc, and the combined organic extracts were washed successively with aqueous NaHCO₃, H₂O and saturated aqueous NaCl and dried. The solvent was removed in vacuo, and the residue was purified by flash chromatography on silica gel to afford the title compound (110 mg, 85%).

e) Ethyl (1 RS)-3-(4-t-Butyldimethylsiloxyphenyl)-1-hydroxy-1-(4-methoxyphenyl)indene-2-carboxylate. To dry magnesium turnings (119 mg, 4.9 mmol) under an argon atmosphere was added, portionwise, a solution of p-bromoanisole (0.61 ml, 4.9 mmol) in 9: 1 Et₂O/THF (10 ml). The resulting p-methoxyphenyl magnesium bromide solution was added to a solution of ethyl 3-(4 t-butyldimethylsiloxyphenyl)-1-oxoindene-2-carboxylate (1.00 g, 2.5 mmol) in Et₂O (60 ml) under an argon atmosphere at 0° C. The resulting mixture was allowed to warm to room temperature and was stirred for 5 min. The mixture was partitioned between 3M HCl and EtOAc. The organic extract was washed successively with H₂O, aqueous NaHCO₃, H₂O and saturated aqueous NaCl and dried. The solvent was removed in vacuo to provide the title compound (1.47 g) which was used without further purification.

f) Ethyl (RS)-1-hydroxy-(4-t-Butyldimethylsiloxyphenyl)-3-(4-methoxyphenyl)indene-2-carboxylate. To a solution of ethyl (1RS)3-(4-t-butyldimethylsiloxyphenyl)-1-hydroxy-1-(4-methoxyphenyl)indene-2-carboxylate (2.5 mmol, prepared above) in CH₂Cl₂ (10 ml) at 0° C. under an argon atmosphere was added triethylsilane (0.48 ml, 3.0 mmol), followed by boron trifluoride etherate (1.8 ml, 14.6 mmol). The reaction mixture was allowed to warm to room temperature and stirred for 10 min, at which time was added slowly 3M HCl. The mixture was extracted with EtOAc. The organic extract was washed successively with H₂O, aqueous NaHCO₃, H₂O and saturated aqueous NaCl and dried. The solvent was removed in vacuo, and the residue was purified by flash chromatography on silica gel, eluting with 15% Et₂O/hexanes to provide the title compound as a mixture of Δ1 and Δ2 double bond isomers (820 mg, 67% for two steps).

g) Ethyl (1RS,2SR,3SR)-1-(4-t-Butyldimethyl-siloxyphenyl)-3-(4-methoxyphenyl)indene-2-carboxylate. To a solution of ethyl (RS)-3-(4-t-butyldimethylsiloxyphenyl)-1-(4-methoxyphenyl)indene-2-carboxylate (mixture of Δ1 and Δ2 double bond isomers) (750 mg, 1.5 mmol) in EtOH (25 ml) was added 5% palladium on activated carbon (70 mg). The resulting suspension was stirred under an atmosphere of H₂ for 18 h, then was filtered through a pad of Celite. The filtrate was concentrated under reduced pressure to afford the title compound (730 mg, 97%), which was used without further purification.

h) Ethyl (1RS,2RS,3SR-1-(4-Hydroxyphenyl)-3-(4-methoxyphenyl)indane-2-carboxylate. To a solution of ethyl (1RS,2SR,3SR)-1-(4-t-butyldimethylsiloxyphenyl)-3-(4methoxyphenyl)indane-2-carboxylate (723 mg, 1.4 mmol) in EtOH (20 ml) was added 1M NaOH (1.6 ml, 1.6 mmol), and the resulting mixture was stirred at room temperature for 30 min. The mixture was then partitioned between 3M HCl and EtOAc. The aqueous phase was extracted with EtOAc, and the combined organic extracts were washed successively with H₂O and saturated aqueous NaCl and dried. The solvent was removed in vacuo to afford the title compound (554 mg, 100%).

i) Ethyl (cis, cis)-1,3-Di(4-methoxyphenyl)indane-2-carboxylate. To a solution of ethyl (1RS,2RS,3SR)-1-(4-hydroxyphenyl)3-(4methoxyphenyl)indane-2-carboxylate (270 mg, 0.7 mmol) in acetonitrile (5 ml) at 0° C. was added 1,8-diazabicyclo[5.4.0]undec-7-ene (0.25 ml, 1.7 mmol), followed by methyl iodide (0.5 ml, 8.0 mmol). The resulting mixture was allowed to warm to room temperature and was stirred overnight. The mixture was partitioned between EtOAc and dilute aqueous HCl. The organic extract was washed with saturated aqueous NaCl and dried. The solvent was removed in vacuo, and the residue was purified by flash chromatography to afford the title compound (40 mg, 32% based on recovered starting material).

j) (trans, trans)-1,3-Di(4-methoxyphenyl)indane-2-carboxylic acid. To a solution of ethyl (cis, cis)-1,3-di (4methoxyphenyl)indane-2-carboxylate (35 mg, 0.09 mmol) in EtOH (3 ml) was added 1M NaOH (0.25 ml, 0.25 mmol), and the resulting mixture was allowed to stir at room temperature overnight. Thin layer chromatographic analysis at this time indicated that the reaction was incomplete, so 5M NaOH (0.15 ml, 0.75 mmol) was added, and the mixture was allowed to stand at 0° C. for 5 days. Water was added, and the mixture was concentrated under reduced pressure. The aqueous residue was extracted with Et₂O (2×), and the Et₂O extracts were discarded. The aqueous phase was acidified with 6M HCl and extracted several times with EtOAc. The combined EtOAc extracts were washed successively with H₂O and saturated aqueous NaCl and dried. The solvent was removed in vacuo to provide an oily residue which crystallized upon standing. The solid material was recrystallized from EtOAc/ hexanes to afford the title compound (19 mg, 59%); m.p. 192–193° C.

¹H NMR (acetone-d₆): δ 7.21–7.18 (m, 2H); 6.92 (dd, 4H, J=6.6 Hz, 2.1 Hz); 6.86–6.83 (m, 2H); 4.59 (d, 2H, J=10 Hz); 3.79 (s, 6H); 3.26 (t, 1H, J=10 Hz). E: 392 [(M+NH₄)⁺].

Anal. Calc. for C₂₄H₂₂O₄: C, 76.99; H, 5.92.

Found C, 76.74; H 6.15.

EXAMPLE 3

(1RS,2SR,3SR)-1-(4-Methoxyphenyl)-3-(3,4-methylenedioxyphenyl)indane-2-carboxylic acid a) 2-(3,4-Methylenedioxybenzoyl)benzoic acid. To a solution of 2-bromobenzoic acid (12 g, 0.06 mol) in THF (200 ml) at −100° C. under an argon atmosphere was added dropwise n-butyl lithium (50 ml of 2.5M solution in hexanes, 0.125 mol), maintaining the temperature below −90° C. Upon completion of the addition, the resulting solution was stirred at −100° C. for 1 h, at which time was added slowly a solution of piperonylic acid chloride (11 g, 0.06 mol) in THF (50 ml), maintaining the temperature below −90° C. The resulting mixture was allowed to warm to −80° C. and stirred for 1 h, then was allowed to slowly warm to room temperature and left to stand for 48 h. The reaction mixture was concentrated under reduced pressure, and the residue was partitioned between $Et_2O$ and 1M HCl. The organic phase was extracted with 10% aqueous NaOH. The NaOH extract was acidified with concentrated HCl, and the combined aqueous material was extracted with $Et_2O$. The $Et_2O$ extract was dried ($MgSO_4$) and concentrated under reduced pressure. The residue was purified by flash chromatography on silica gel, eluting with a solvent gradient of 10–30% EtOAc/0. 1% HOAc/hexanes to afford the title compound as an off-white solid (4.5 g, 28%).

b) Diethyl 2-[2-(3,4-Methylenedioxybenzoyl)benzoyl-malonate. A solution of 2-(3,4-methylenedioxybenzoyl)-benzoic acid (4.0 g, 14.8 mmol) in thionyl chloride (30 ml) was heated at reflux for 2 h, then allowed to cool and was concentrated under reduced pressure. The residue was dissolved in $Et_2O$ (50 ml) and to this was added a solution of diethyl magnesium malonate [prepared by the method of Walker and Hauser, JACS, 68, 1386 (1946) using magnesium (0.8 g, 33.3 mmol) and diethyl malonate (4.9 g, 30.6 mmol)] in $Et_2O$. The resulting mixture was heated at reflux for 1 h, then allowed to cool and was poured into ice-cold 10% aqueous $H_2SO_4$ (100 ml). The aqueous phase was extracted with $Et_2O$, and the combined organic material was washed with saturated aqueous NaCl and dried. The solvent was removed under reduced pressure to afford the title compound as an orange oil, which was used without further purification.

c) Ethyl 3-(3,4-Methylenedioxyphenyl)-1-oxoindene-2-carboxylate. A solution containing diethyl 2-[2-(3,4-methylenedioxybenzoyl)benzoylmalonate (crude material prepared above) in 5% aqueous $Na_2CO3$ (100 ml) was heated at reflux for 10 min. The reaction mixture was then allowed to cool, and the aqueous material was removed by decantation. The residue was placed in $H_2O$ (50 ml), and the mixture was heated at reflux, cooled and concentrated under reduced pressure. The residue was recrystallized from hexanes to afford the title compound as a yellow solid (5.0 g, 100% for two steps).

d) Ethyl (1RS) 1-Hydroxy-1-(methoxyphenyl)-3-(3,4-methylenedioxyphenyl)indene-2-carboxylate, A solution of 4-bromoanisole (0.89 g, 5.0 mmol) in 9:1 $Et_2O$/THF (10 ml) was added to magnesium turnings (0.105 g, 5.0 mmol), and the resulting mixture was allowed to stir for 30 min. The resultant 4-methoxyphenyl magnesium bromide was added dropwise to a solution of ethyl 3-(3,4-methylenedioxyphenyl)1-oxoindene-2-carboxylate (0.77 g, 2.4 mmol) in 10: 1 $Et_2O$/ THF (55 ml) at 0° C. The resulting mixture was stirred at 0° C. for 1 h and was then partitioned between EtOAc and 1M HCl. The aqueous phase was extracted with EtOAc, and the combined organic extracts were washed successively with 5% aqueous $NaHCO_3$ and saturated aqueous NaCl and dried ($MgSO_4$). The solvent was removed under reduced pressure, and the residue was purified by flash chromatography on silica gel, eluting with 10% EtOAc/hexanes to afford the title compound as a yellow glassy solid (0.80 g, 80%).

e) Ethyl (RS)-1-(4-Methoxyphenyl)-3-(3,4-methylenedioxyphenyl)indene-2-carboxylate. To a solution of ethyl (1RS)-1-hydroxy-1-(4-methoxyphenyl)-3-(3,4-methylenedioxyphenyl)-indene-2-carboxylate (0.80 g, 1.9 mmol) in $CH_2Cl_2$ (10 ml) at 0° C. under an argon atmosphere was added triethylsilane (0.28 g, 2.4 mmol), followed by boron trifluoride etherate (1 ml, 8.1 mmol). The resulting solution was stirred at 0° C. for 10 min, and was then partitioned between EtOAc and 3M HCl. The organic extract was washed with saturated aqueous NaCl and dried ($MgSO_4$). The solvent was removed in vacuo, and the residue was filtered through a pad of silica gel, eluting with $CH_2Cl_2$. The title compound (mixture of Δ1 and Δ2 double bond isomers) was obtained as a glassy, yellow solid (0.72 g, 94%).

f) Ethyl (1RS,2RS,3SR)-1-(4Methoxyphenyl)-3-(3,4-methylenedioxyphenyl)indane-2-carboxylate. To a solution of ethyl (RS)-1-(4-methoxyphenyl)-3-(3,4methylenedioxyphenyl)-indene-2-carboxylate (0.72 g, 1.7 mmol) in EtOH (30 ml) was added 10% palladium on activated carbon (1 g). The resulting suspension was stirred under an atmosphere of $H_2$ for 56 h and filtered. The filtrate was concentrated under reduced pressure to afford the title compound as a yellow solid (0.70 g, 95%), which was used without further purification.

g) (1RS,2SR,3SR) 1-(4-Methoxyphenyl)-3-(3,4-methylenedioxyphenyl)indane-2-carboxylic acid, To a solution of ethyl (1RS,2RS,3SR)-1-(4-methoxyphenyl)-3-(3,4-methylenedioxyphenyl)indane-2-carboxylate (0.10 g, 0.2 nmol) in EtOH (5 ml) was added a solution of sodium hydroxide (0.10 g, 2.5 mmol) in $H_2O$ (2 ml). The resulting mixture was stirred at room temperature overnight. The mixture was acidified, and the solid which formed was collected by filtration and dried under reduced pressure to afford the title compound as a tan solid (0.04 g, 86%).

$^1$H NMR ($CDCl_3$): δ 7.25 (m, 5H); 6.90 (m, 4H); 6.77 (d, 2H, J=7 Hz); 5.95 (m, 2H); 4.61 (d, 2H, J=10 Hz); 3.81 (s, 3H); 3.25 (t, 2H, J=10 Hz). MS: 387 [(M—H$^+$).

Anal. Calc. for $C_{24}H_{20}O_5 \cdot \frac{1}{8} H_2O$: C, 73.79; H, 5.22. Found C, 76.73; H 5.21.

EXAMPLE 4

(1RS,2SR,3SR)-1-(4-Fluorophenyl)-3-(3,4-methylenedioxyphenyl)indane-2-carboxylic acid a) Ethyl (1RS)-1-(4-Fluorophenyl)-1-hydroxy-3-(3,4-methylenedioxyphenyl)indene-2-carboxylate. To a solution of ethyl 3-(3,4-methylenedioxyphenyl)-1-oxoindene-2-carboxylate (100 mg, 0.31 mmol) in THF (5 ml) under an argon atmosphere at 0° C. was added a solution of freshly prepared 4-fluorophenyl magnesium bromide (0.62 mmol). After stirring for 45 min, the mixture was partitioned between 3M HCl and EtOAc. The organic extract was washed successively with $H_2O$, 5% aqueous $NaHCO_3$ and saturated aqueous NaCl. The solvent was removed in vacuo, and the residue was purified by flash chromatography, eluting with 15% EtOAc/hexanes to afford the title compound (45 mg, 35%).

b) Ethyl (RS-1-(Fluorophenyl)-3-(3,4-methylenedioxyphenyl)indene-2-carboxylate. To a solution of ethyl (1RS)-1-(4-fluorophenyl)-1-hydroxy-3-(3, 4methylenedioxyphenyl)indene-2-carboxylate (45 mg, 0.11 mmol) in $CH_2Cl_2$ (3 ml) at 0° C. was added triethylsilane (38 μl, 0.24 mmol), followed by boron trifluoride etherate (121 μl, 0.98 mmol). The reaction mixture was allowed to warm to room temperature and stirred for 15 min, at which time was added slowly 3M HCl. The mixture was extracted with EtOAc. The organic extract was washed successively with $H_2O$, 5% aqueous $NaHCO_3$ and saturated aqueous NaCl. The solvent was removed in vacuo to provide the title compound (40 mg, 90%) as a mixture of Δ1 and Δ2 double bond isomers.

c) Ethyl (1RS,2RS,3SR)-1-(4-Fluorophenyl)-3-(3,4-methylenedioxyphenyl)indane-2-carboxylate. To a solution of ethyl (RS)-1-(4-fluorophenyl)-3-(3,4-methylenedioxyphenyl)indene-2-carboxylate (40 mg, 0.10 mmol) in EtOH (3 ml) was added 10% palladium on activated carbon (45 mg). The resulting suspension was stirred under an atmosphere of $H_2$ overnight, then was filtered through a pad of Celite. The filtrate was concentrated under reduced pressure to afford the title compound (40 mg, 100%), which was used without further purification.

d) (1RS,2SR,3SR)-1-(4-Fluorophenyl)-3-(3,4-methylenedioxyphenyl)indane-2-carboxylic acid. To a solution of ethyl (1RS, 2RS, 3SR)-1-(4-fluorophenyl)-3-(3,4-methylenedioxyphenyl)indane-2-carboxylate (60 mg, 0. 15 mmol) in EtOH (0.5 ml) was added 6M KOH (0.14 ml, 0.84 mmol). The resulting mixture was allowed to stir at room temperature overnight, then was concentrated under reduced pressure. The residue was partitioned between $H_2O$ and $Et_2O$. The aqueous phase was acidified with 3M HCl and extracted several times with EtOAc. The combined EtOAc extracts were washed successively with $H_2O$ and saturated aqueous NaCl and dried ($MgSO_4$). The solvent was removed in vacuo to afford an oil, which was crystallized from EtOAc/ hexanes. The title compound was obtained as an off-white crystalline solid (22 mg, 39%); m.p. 146–149° C.

$^1$H NMR (CDCl$_3$): δ 7.23 (m, 4H); 6.96 (m, 1H); 6.90 (m, 1H); 6.79 (s, 2H); 6.75 (s, 1H); 5.96 (m, 2H); 4.62 (apparent br t, 2H, J=10 Hz); 3.25 (t, 1H, J=10 Hz).

MS m/e (rel. int.): 753 ((2M+1)$^+$, 3].

Anal. Calcd. for $C_{23}H_{17}FO_4$: C, 73.40; H, 4.55.

Found: C, 73.19; H, 4.45.

EXAMPLE 5

(1RS,2SR,3SR)-1-(3-Methoxyphenyl)-3-(3,4-methylenedioxyphenyl)indane-2-carboxylic acid a) Ethyl (1RS)-1-Hydroxy-1-(3-methoxyphenyl)-3-(3,4-methylenedioxyphenyl)indene-2-carboxylate. To a solution of ethyl 3-(3,4-methylenedioxyphenyl)-1-oxoindene-2-carboxylate (100 mg, 0.31 mmol) in THF (2 ml) under an argon atmosphere at 0° C. was added a solution of freshly prepared 3-methoxyphenyl magnesium bromide (0.31 mmol). After stirring for 15 min, additional 3-methoxyphenyl magnesium bromide (0.06 mmol) was added. Stirring was continued for 45 min, at which time thin layer chromatographic analysis indicated that the reaction was incomplete. Additional 3-methoxyphenyl magnesium bromide (0.12 mmol) was added. After string for 2 h more, the mixture was partitioned between 3M HCl and EtOAc. The organic extract was washed successively with $H_2O$, 5% aqueous $NaHCO_3$, $H_2O$ and saturated aqueous NaCl. The solvent was removed in vacuo, and the residue was purified by flash chromatography, eluting with 15% EtOAc/ hexanes to afford the title compound (150 mg, 100%).

b) Ethyl (1RS)-1-(3-Methoxyphenyl)-3-(3,4methylenedioxyphenyl)indene-2-carboxylate. To a solution of ethyl (1RS)-1-hydroxy-1-(3-methoxyphenyl)-3-(3,4-methylenedioxyphenyl)-indene-2-carboxylate (150 mg, 0.35 mmol) in $CH_2Cl_2$ was added triethylsilane (67 μl, 0.42 mmol), followed by boron trifluoride etherate (213 μl, 1.73 mmol). The reaction mixture was allowed to stir for 30 min, at which time was added slowly 5% aqueous HCl. The mixture was extracted with EtOAc. The organic extract was washed successively with $H_2O$, 5% aqueous $NaHCO_3$, $H_2O$ and saturated aqueous NaCl and dried ($MgSO_4$). The solvent was removed in vacuo, and the residue was purified by flash chromatography, eluting with 10% EtOAc/hexanes to provide the title compound (45 mg, 31%) as a mixture of Δ1 and Δ2 double bond isomers.

c) Ethyl (1RS,2RS,3SR)-1-(3-Methoxyphenyl)-3-(3,4-methylenedioxyphenyl)indane-2-carboxylate, To a solution of ethyl (RS)-1-(3-methoxyphenyl)-3-(3,4-methylenedioxyphenyl)indene-2-carboxylate (45 mg, 0.11 mmol) in EtOH (3 ml) was added 10% palladium on activated carbon (45 mg). The resulting suspension was shaken on a Parr hydrogenator at 50 psi $H_2$ overnight, then was filtered through a pad of Celite. The filtrate was concentrated under reduced pressure to afford the title compound (43 mg, 94%), which was used without further purification.

d) (1RS,2SR,3SR)-1-(3-Methoxyphenyl)-3-(3,4-methylenedioxyphenyl)indane-2-carboxylic acid. To a solution of ethyl (1RS,2RS,3SR)-1-(3-methoxyphenyl)-3-(3,4-methylenedioxyphenyl)indane-2-carboxylate (43 mg, 0.10 mmol) in EtOH (1 ml) was added 6M KOH (0.10 mL, 0.60 mmol). The resulting mixture was allowed to stir at room temperature overnight, then was partitioned between $H_2O$ and $Et_2O$. The aqueous phase was acidified with 3M HCl and extracted several times with EtOAc. The combined EtOAc extracts were washed successively with $H_2O$ and saturated aqueous NaCl and dried ($MgSO_4$). The solvent was removed in vacuo to afford an oil, which was crystallized from $Et_2O$/ hexanes. The title compound was obtained as a solid; m.p. 131–133° C.

$^1$H NMR (CDCl$_3$): δ 7.21 (m, 3H); 6.97–6.73 (m, 8H); 5.95 (m, 2H); 4.61 (apparent br t, 2H, J=9 Hz); 3.67 (s, 3H); 3.30 (t, 1H, J=9 Hz).

MS m/e (rel. int.): 777 [(2M+1)$^+$, 65].

Anal. Calcd. for $C_{24}H_{20}O_5$: C, 74.21; H, 5.19.

Found: C, 74.71; H, 5.47.

EXAMPLE 6

(1RS,3RS)-1,3-Di-(3,4-methylenedioxyphenyl)-indane-2-carboxylic acid a) Ethyl(1RS)-1,3-di-(3,4-methylenedioxyphenyl)-1-hydroxyindene-2-carboxylate. To dry magnesium turnings (0.25 g, 10 mmol) under an argon atmosphere was added a solution of 4-bromo- 1,2-methylenedioxybenzene (2.1 g, 10 mmol) in 1: 10 THF $Et_2O$ (22 ml). The resulting solution was allowed to stir at room temperature for 2 h. During this time, additional THF (4 ml) was added. The resulting 3,4-methylenedioxyphenylmagnesium bromide was added to a solution of ethyl 3-(3,4-methylenedioxyphenyl)-1-oxoindene-2-carboxylate (0.50 g, 2 mmol) in 1:4 THF/ $Et_2O$ (25 ml) under an argon atmosphere at 0° C. The resulting mixture was stirred at 0° C. for 15 min, at which time 1M HCl (50 ml) was added. The phases were separated and the aqueous phase was extracted with $Et_2O$. The combined organic extracts were washed with saturated aqueous NaCl and dried ($MgSO_4$). The solvent was removed in vacuo, and the residue was purified by flash chromatography, eluting with 10% EtOAc/hexanes to afford the title compound as a yellow solid (0.29 g, 42%).

b) Ethyl(RS)-1,3-Di-(3,4-methylenedioxyphenyl)indene-2-carboxylate. To a solution of ethyl (1RS)-1,3-di-(3,4-methylenedioxyphenyl)-1-hydroxyindene-2-carboxylate (0.29 g, 0.65 mmol) in $CH_2Cl_2$ (3 ml) at 0° C. under an argon atmosphere was added triethylsilane (91 mg, 0.78 mmol), followed by boron trifluoride etherate (0.3 ml, 2.4 mmol). The reaction mixture was stirred for 10 min, at which time was added ice-cold 1M HCl, and the mixture was extracted with EtOAc. The organic extract was washed with saturated aqueous NaCl and dried ($MgSO_4$). The solvent was removed in vacuo, and the residue was placed on a small pad of silica gel, eluting with $CH_2CL_2$ to provide the title compound (257 mg, 92%).

c) Ethyl (1RS,3RS)-1,3-Di-(3,4-methylenedioxy-phenyl) indane-2-carboxylate. Ethyl(RS)-1,3-di-(3,4-Methylenedioxyphenyl)indene-2-carboxylate (163 mg, 0.38 mmol) was placed in MeOH (0.05 ml), and to this was added $SmI_2$ (10 ml of 0.1M solution in THF, 1.0 mmol). The resulting mixture was stirred under an argon atmosphere overnight, at which time thin layer chromatographic analysis indicated that the reaction was incomplete. Additional $SmI_2$ (5ml of 0.1M solution in THF, 0.5 mmol) was added, and stirring was continued for 2 h. The reaction mixture was partitioned between $Et_2O$ and 5% aqueous $Na_2S_2O_3$. The organic extract was washed with saturated aqueous NaCl and dried ($MgSO_4$). The solvent was removed under reduced pressure, and the residue was purified by flash chromatography, eluting with 10% EtOAc/ hexanes to afford the title compound as a colorless, glassy solid (120 mg, 75%).

d) (1RS,3RS)-1,3-Di-(3,4methylenedioxyphenyl)indane-2-carboxylic acid. To a solution of ethyl (1RS, 3RS)-1,3-di-(3,4-methylenedioxyphenyl)indane-2-carboxylate (75 mg, 0.17 mmol) in EtOH (20 ml) was added NaOH (0.10 g, 2.5 mmol). The resulting mixture was allowed to stir at room temperature for 3 d, at which time thin layer chromatographic analysis indicated that the reaction was incomplete. The mixture was then heated at reflux for 36 h, allowed to cool and was concentrated under reduced pressure. To the residue was added concentrated HCl, and the solid which formed was collected by filtration and dried. The solid was triturated with boiling hexanes to afford the title compound as a white solid (50 mg, 73%); m.p. 182–185° C.

$^1$H NMR ($CDCl_3$): δ 7.25 (m, 2H); 7.15 (m, 1H); 7.00 (m, 1H); 6.76 (s, 2H); 6.68 (m, 2H); 6.50 (dd, 1H, J=8, 1 Hz); 6.40 (d, 1H, J=2 Hz); 5.94 (s, 2H); 5.90 (d, 1H, J=1 Hz); 5.87 (d, 1H, J=1 Hz); 4.84 (d, 1H, J=10 Hz); 4.78 (d, 1H, J=10 Hz); 3.63 (dd, 1H, J=10 Hz, 9 Hz).

MS: 402 (M)$^+$.

Calcd. for $C_{24}H_{18}O_6 \cdot ⅓ H_2O$: C, 71.00; H. 4.52. Found: C, 71.13; H, 4.46.

EXAMPLE 7

(trans,trans)-1,3-Di-(3,4-methylenedioxyphenyl)indane-2-carboxylic acid a) Ethyl (cis,cis)-1,3-Di-(3,4-methylenedioxyphenyl) indane-2-carboxylate. To a solution of ethyl (RS)-1,3di-(3,4methylenedioxyphenyl)indene-2-carboxylate (93 mg, 0.22 mmol) in EtOH (2 ml) was added 10% palladium on activated carbon (0.10 g). The resulting suspension was shaken on a Pair hydrogenator at 55 psi $H_2$ for 2 d, then was filtered through a pad of Celite. The filtrate was concentrated under reduced pressure to afford the title compound (45 mg, 48%) as a glassy, yellow solid, which was used without further purification.

b) (trans, trans)- 1,3-Di-(3,4methylenedioxyphenyl) indane-2-carboxylic acid. To a solution of ethyl (cis, cis)1, 3di-(3,4-methylenedioxyphenyl)indane-2-carboxylate (45 mg, 0.1 mmol) in 2: 1 EtOH/$H_2O$ (15 ml) was added sodium hydroxide (50 mg, 1.2 mmol). The resulting solution was allowed to stir at room temperature overnight, then was concentrated under reduced pressure. The residue was treated with concentrated HCl, and the solid which formed was collected by filtration and dried. The solid was recrystallized from $Et_2O$/hexanes to afford the title compound as a light tan solid (12 mg, 30%); m.p. 188–191° C.

EXAMPLE 8

(1RS,2RS,3SR)-1-(3,4-Methylenedioxyphenyl)-3-phenylindane-2-carboxylic acid a) Ethyl (1RS)- 1-Hydroxy-1-(3,4-methylenedioxyphenyl)-3-phenylindene-2-carboxylate. To a solution of ethyl 1-oxo-3-phenylindene-2-carboxylate (1.0 g, 3.6 mmol) in THF (35 ml) under an argon atmosphere at 0° C. was added a solution of freshly prepared 3,4-methylenedioxyphenyl magnesium bromide (5.4 mmol). After stirring for 30 min, the mixture was partitioned between 3M HCl and EtOAc. The organic extract was washed successively with $H_2O$, 5% aqueous $NaHCO_3$ and saturated aqueous NaCl and dried ($MgSO_4$). The solvent was removed in vacuo, and the residue was purified by flash chromatography, eluting with 10% EtOAc/ hexanes to afford the title compound (1.03 g, 72%).

b) Ethyl (RS)-1-(3,4-Methylenedioxyphenyl)-3-phenylindene-2-carboxylate. To a solution of ethyl (1RS)l-hydroxy-1-(3,4-methylenedioxyphenyl)3-phenylindene-2-carboxylate (1.03 g, 2.58 mmol) in $CH_2Cl_2$ (40 mL) was added triethylsilane (0.49 ml, 3.07 mmol), followed by boron trifluoride etherate (1.55 ml, 12.6 mmol). The reaction mixture was allowed to stir for 15 min, at which time was added slowly 3M HCl. The mixture was extracted with EtOAc. The organic extract was washed successively with $H_2O$, 5% aqueous $NaHCO_3$ and saturated aqueous NaCl. The solvent was removed in vacuo to provide the title compound (1.00 g, 100%) as a mixture of Δ1 and Δ2 double bond isomers.

c) Ethyl (1RS,2SR,3SR)-1-(3,4-Methylenedioxyphenyl)-3-phenylindane-2-carboxylate. To a solution of ethyl (RS)-1-(3,4-methylenedioxyphenyl)-3-phenylindene-2-carboxylate (1.00 g, 2.60 mmol) in EtOH (25 ml) was added 10% palladium on activated carbon (30 mg). The resulting suspension was stirred under an atmosphere of $H_2$ overnight. Thin layer chromatographic analysis indicated that the reaction was incomplete, so additional 10% palladium on activated carbon (30 mg) was added, and the mixture was shaken on a Parr hydrogenator at 30 psi $H_2$ for 2 d. At this time, thin layer chromatographic analysis again indicated that the reaction was incomplete. The reaction mixture was filtered through a pad of Celite, and 10% palladium on activated carbon (250 mg) was added. The reaction mixture was shaken on a Parr hydrogenator at 60 psi $H_2$ overnight. Filtration and repetition of the latter hydrogenation conditions led to complete consumption of starting material. The reaction mixture was filtered through a pad of Celite, and the filtrate was concentrated under reduced pressure to afford the title compound (650 mg, 65%), which was used without further purification.

d) (1RS,2RS,3SR)-1-(3,4Methylenedioxyphenyl)-3-phenylindane-2-carboxylic MW. To a solution of ethyl (1RS, 2SR, 3SR)-1-(3,4methylenedioxyphenyl)-3-phenylindane-2-carboxylate (650 mg, 1.68 mmol) in EtOH containing a few drops of THF was added 6M KOH (1.68 ml, 10.1 mmol). The resulting mixture was allowed to stir at room temperature overnight, then was concentrated under reduced pressure. The residue was partitioned between $H_2O$ and $Et_2O$. The aqueous phase was acidified with 3M HCl and extracted several times with EtOAc. The combined EtOAc extracts were washed successively with $H_2O$ and saturated aqueous NaCl and dried (MgSO$_4$). The solvent was removed in vacuo to afford an oil, which was crystallized from EtOAc/hexanes. The title compound was obtained as a solid (305 mg, 51%); m.p. 186–187° C.

Anal. Calcd. for C$_{23}$H$_{18}$O$_4$: C, 77.08; H, 5.06.

Found: C, 76.60; H, 5.08.

EXAMPLE 9

(1RS,2SR,3SR)-1-(4-Methoxyphenyl)-3-(3,4-methylenedioxyphenyl)-2-(tetrazol-5-yl)indane a) (1RS,2SR,3SR)-1-(4-Methoxyphenyl)-3-(3,4-methylenedioxyphenyl)indane-2-carboxamide. A mixture of (1RS, 2SR, 3SR)-1-(4-methoxyphenyl)-3-(3,4-methylenedioxyphenyl)indane-2-carboxylic acid (250 mg, 0.64 mmol) in SOCl$_2$ (2.5 ml) was allowed to stir overnight under an argon atmosphere. The reaction mixture was concentrated under reduced pressure, and the residue was dissolved in benzene (5 ml). To the resulting mixture under an argon atmosphere was added concentrated NH$_4$OH (5 ml). The solid which formed was collected by filtration, washed with H$_2$O and dried in vacuo to afford the title compound (185 mg, 75%). b) (1RS,2SR. 3SR)-1-(4-Methoxyphenyl)-3-(3,4methylenedioxyphenyl)indane-2-carbonitrile. To ice-cold DMF (1 ml) under an argon atmosphere was added oxalyl chloride (68 ml, 0.78 mmol). After stirring for 5 min at 0° C., a solution of (1RS, 2SR, 3SR)-1-(4-methoxyphenyl)-3-(3,4-methylenedioxyphenyl)indane-2-carboxamide (150 mg, 0.39 mmol) in DMF (2 ml) was added, and stirring was continued for an additional 10 min at 0° C. The reaction mixture was partitioned between EtOAc and 3M HCl. The aqueous phase was extracted with EtOAc, and the combined organic extracts were washed successively with H$_2$O, aqueous NaHCO$_3$, H$_2$O and saturated aqueous NaCl and dried. The solvent was removed in vacuo to afford the title compound as a white solid (135 mg, 94%) which was used without further purification.

c) (1RS,2SR. 3SR)-1-(4-Methoxyphenyl)-3-(3,4-methylenedioxyphenyl)-2-(tetrazol-5-yl)indane. To THF (2.5 ml) at −78° C. under an argon atmosphere was added aluminum chloride (90 mg, 0.67 mmol). After slowly warming to room temperature, sodium azide (130 mg, 2.2 mmol) was added, and the resulting mixture was heated at 70° C. for 5 min, then cooled to room temperature. To the reaction mixture was added a solution of (1RS, 2SR, 3SR)-1-(4-methoxyphenyl)3-(3,4-methylenedioxyphenyl)indane-2-carbonitrile (125 mg, 0.34 mmol) in THF (2.5 ml). After heating at 70° C. overnight, thin layer chromatographic analysis of the reaction mixture indicated the presence of starting material, so additional Al(N$_3$)$_3$ was prepared as above (1.34 mmol) in THF. To this was added the reaction mixture, and heating at 70° C. was resumed for an additional 5 h. The mixture was partitioned between EtOAc and 3M HCl. The aqueous phase was extracted with EtOAc, and the combined organic extracts were washed successively with H$_2$O and saturated aqueous NaCl and dried. The solvent was removed in vacuo, and the residue was crystallized from EtOAc/hexanes to afford the title compound (78 mg, 56%). A portion of this material was further purified by MPLC (LiChroprep RP-18, MeOH/H$_2$O=60/40) and then recrystallized; m.p. 155–157° C. (EtOAc/hexanes).

$^1$H NMR (CDCl$_3$): δ 7.28–7.15 (m, 4H); 7.03–6.95 (m, 2H); 6.87–6.84 (m, 2H); 6.74 (s, 3H); 5.94 (d, 1H, J=1.2 Hz); 5.92 (d, 1H, J=1.2 Hz); 4.79 (d, 1H, J=11.6 Hz); 4.73 (d, 1H, J=11.6 Hz); 3.79 (S, 3H); 3.65 (t, 1H, J=11.6 Hz). MS (m/e): 413.2 [(M+H)$^+$].

EXAMPLE 10

(1RS,2SR,3RS)-1-(2-Methoxyphenyl)-3-(3,4-methylenedioxyphenyl)indane-2-carboxylic acid a) Ethyl (1RS)-1-Hydroxy-1-(2-methoxyphenyl)-3-(3,4-methylenedioxyphenyl)indene-2-carboxylate. To dry magnesium turnings (81 mg, 3,4 mmol) under an argon atmosphere was added a solution of 2-bromoanisole (0.64 g, 3.4 mmol) in 5:1 THF/Et$_2$O (3 ml). A portion of the resulting 2-methoxyphenyl magnesium bromide solution (0.45 ml, 0.51 mmol) was added dropwise to a solution of ethyl 3-(3,4-methylenedioxyphenyl)-1-oxoindene-2-carboxylate (100 mg, 0.34 mmol) in THF (6 ml) under an argon atmosphere at 0° C. After stirring for 15 min, the mixture was partitioned between 3M HCl and EtOAc. The organic extract was washed successively with H$_2$O, 5% aqueous NaHCO$_3$, H$_2$O and saturated aqueous NaCl. The solvent was removed in vacuo, and the residue was purified by flash chromatography, eluting with 15% EtOAc/hexanes to afford the title compound. (100 mg, 68%).

b) Ethyl (RS)-1-(2-Methoxyphenyl)-3-(3,4-methylenedioxyphenyl)indene-2-carboxylate. To a solution of ethyl (1RS)-1-hydroxy-1-(2-methoxyphenyl)-3-(3,4-methylenedioxyphenyl)indene-2-carboxylate (100 mg, 0.23 mmol) in CH$_2$Cl$_2$ (5 ml) was added triethylsilane (32 mg, 0.28 mmol), followed by boron trifluoride etherate (0.13 ml, 1.05 mmol). The reaction mixture was allowed to warm to room temperature and stirred for 10 min, at which time was added slowly 3M HCl. The mixture was extracted with EtOAc. The organic extract was washed successively with H$_2$O, 5% aqueous NaHCO$_3$, H$_2$O and saturated aqueous NaCl and dried (MgSO$_4$). The solvent was removed in vacuo to provide the title compound (91 mg, 96%) as a mixture of Δ1 and Δ2 double bond isomers.

c) Ethyl (1RS,2RS,3RS)-1-(2-Methoxyphenyl)-3-(3,4-methylenedioxyphenyl)indane-2-carboxylate. To a solution of ethyl (RS)-1-(2-methoxyphenyl)-3-(3,4-methylenedioxyphenyl)indene-2-carboxylate (90 mg, 0.22 mmol) in EtOH (10 ml) was added 10% palladium on activated carbon (90 mg). The resulting suspension was shaken on a Parr hydrogenator at 60 psi H$_2$ overnight, then was filtered through a pad of Celite. The filtrate was concentrated under reduced pressure to afford the title compound (90 mg, 100%), which was used without further purification.

d) (1RS,2SR, 3RS)-1-(2-Methoxyphenyl)-3-(3,4methylenedioxyphenyl)indane-2-carboxylic acid. To a solution of ethyl (1RS, 2RS, 3RS)-1-(2-methoxyphenyl)-3-(3,4-methylenedioxyphenyl)indane-2-carboxylate (90 mg, 0.22 mmol) in EtOH (2 ml) containing a few drops of THF was added 6M KOH (0.22 ml, 1.32 mmol). The resulting mixture was allowed to stir at room temperature overnight, then was concentrated under reduced pressure. The residue was partitioned between H$_2$O and Et$_2$O. The aqueous phase was acidified with 3M HCl and extracted with EtOAc. The EtOAc extract was washed successively with H$_2$O and saturated aqueous NaCl and dried MgSO$_4$). The solvent was removed in vacuo to afford the title compound (40 mg, 49%).

$^1$H NMR (CDCl$_3$): δ 7.37–6.73 (m, 11H); 5.93 (m, 2H); 5.03 (d, 1H, J=10 Hz); 4.67 (d, 1H, J=10 Hz); 3.70 (s, 3H); 3.38 (t, 1H, J=10 Hz).

EXAMPLE 11

(1RS,2SR,3SR)-5-Hydroxy-3-(4-methoxyphenyl)-1-(3,4-methyenedioxyphenyl)indane-2-carboxylic acid, sodium salt a) 3-Benzyloxyacetophenone. To a mixture of sodium hydride (4.5 g of 80% mineral oil dispersion, 0.15 mol), which had been washed free of mineral oil, in DMF (25 ml) was added, dropwise with cooling, a solution of 3-hydroxyacetophenone (20.5 g, 0.15 mol) in DMF (25 ml). Upon completion of the addition, the mixture was allowed to stir at room temperature for 15 min, at which time was added benzyl bromide (25.6 g, 0.15 mol). The resulting mixture was allowed to stir at room temperature overnight, then was partitioned between EtOAc and 3M HCl. The aqueous phase was extracted with EtOAc, and the combined organic extracts were washed successively with 1M NaOH, $H_2O$ and saturated aqueous NaCl and dried. The solvent was removed in vacuo to afford the title compound (33 g, 97%), which was used without further purification.

b) Methyl 2-(3-Benzyloxy)benzoylacetate. To a mixture of sodium hydride (28.3 g of 80% mineral oil dispersion, 0.94 mol), which had been washed free of mineral oil, in dimethyl carbonate (100 ml) under an argon atmosphere was added, over 30 min, a solution of 3-benzyloxyacetophenone (92.3 g, 0.41 mol) in dimethyl carbonate (150 ml). Upon completion of the addition, the mixture was heated at reflux for 30 min, then was cooled in an ice bath and quenched by the slow addition of 3M HCl. The mixture was partitioned between EtOAc and 3M HCl, and the aqueous phase was extracted with EtOAc. The combined organic extracts were washed successively with $H_2O$, aqueous $NaHCO_3$, $H_2O$ and saturated aqueous NaCl and dried. The solvent was removed in vacuo to afford the title compound (112.5 g, 97%).

c) Methyl 2-(3-Benzyloxybenzoyl)-3-(3,4-methylenedioxyphenyl)propenoate. A mixture containing methyl 2-(3-benzyloxy)benzoylacetate (75.0 g, 0.26 mol), piperonal (43.6 g, 0.29 mol), acetic acid (3.6 ml) and piperidine (1.2 mls) in benzene (70 mnl) was heated at reflux, with azeotropic removal of $H_2O$. After heating at reflux for 4 h, the reaction mixture was concentrated in vacuo, and the residue was crystallized from EtOH to afford the title compound (93.5 g, 85%); m.p. 116–118° C.

d) Methyl (1RS,2SR)-5-Benzyloxy-1-(3,4-methylenedioxyphenyl)-3-oxoindane-2-carboxylate. To trifluoroacetic acid (150 ml) at 0° C. under an argon atmosphere was added methyl 2-(3-benzyloxybenzoyl)-3-(3,4-methylenedioxyphenyl)propenoate (80.0 g, 0.19 mol). The mixture was allowed to warm to room temperature and stirred for 30 min, at which time the mixture was concentrated under reduced pressure. The residue was dissolved in EtOAc and washed successively with aqueous $NaHCO_3$, $H_2O$ and saturated aqueous NaCl and dried. The solvent was removed in vacuo, and the oily residue was crystallized from EtOAc/ hexanes to afford the title compound (51.3 g, 64%); m.p. 148–150° C.

e) Methyl 5-Benzyloxy-1-(3,4methylenedioxybenyl)-3-oxoindene-2-carboxylate. To a solution of methyl 5benzyloxy-1-(3,4methylenedioxyphenyl)-3-oxoindane-2-carboxylate (27.3 g, 65.6 mmol) in benzene (90 ml), cooled in an ice-$H_2O$ bath, was added 2,3-dichloro-5,6-dicyano-1,4benzoquinone (15.4 g, 67.8 mmol). The resulting mixture was stirred at 0° C. for 1 h, allowed to warm to room temperature for 1.5 h, and finally warmed to 40° C. for 1 h. The solid which formed was removed by filtration and washed with benzene. The combined filtrate and washings were poured into EtOAc (200 ml) and washed successively with aqueous $Na_2CO_3$ (3×), $H_2O$ (3×), 3M HCl, $H_2O$ (3×) and saturated aqueous NaCl and dried. The solvent was removed in vacuo, and the residue was crystallized from EtOAc/ hexanes to afford the title compound (16.4 g, 60%) as a red crystalline solid; m.p. 140–141° C.

f) Methyl (3RS)-5-Benzyloxy-3-hydroxy-3-(4-methoxyphenyl)-1-(3,4-methylenedioxyphenyl)indene-2-carboxylate.

To dry magnesium turnings (0.96 g, 40 mmol) under an argon atmosphere was added a solution of 4-bromoanisole (7.48 g, 40 mmol) in 9:1 $Et_2O$/THF (50 ml). The resulting 4methoxyphenyl magnesium bromide solution was added portionwise to a solution of methyl 5-benzyloxy-1-(3,4-methylenedioxyphenyl)-3-oxoindene-2-carboxylate (8.29 g, 20 mmol) in THF (250 ml) under an argon atmosphere. Upon completion of the addition, the mixture was quenched by the addition of 3M HCl and extracted with EtOAc. The organic extract was washed successively with $H_2O$, aqueous $NaHCO_3$, $H_2O$ and saturated aqueous NaCl. The solvent was removed in vacuo to afford the title compound (11.58 g, 100%), which was used without further purification.

g) Methyl (RS)-5-Benzyloxy-3-(4methoxyphenyl)-1-(3,4-methylenedioxyphenyl)indene-2-carboxylate. To a solution of methyl (3RS)-5-benzyloxy-3-hydroxy-3-(4-methoxyphenyl)-1-(3,4-methylenedioxyphenyl)indene-2-carboxylate (crude material prepared above) in $CH_2Cl_2$ (75 ml) under an argon atmosphere at 0° C. was added triethylsilane (3.9 ml, 23.6 mmol), followed by boron trifluoride etherate (14.7 ml, 120 mmol). The reaction mixture was stirred for 10 min at 0° C., at which time the mixture was partitioned between 3M HCl and EtOAc. The organic extract was washed successively with $H_2O$, aqueous $NaHCO_3$, $H_2O$ and saturated aqueous NaCl and dried. The solvent was removed in vacuo, and the residue was purified by flash chromatography, eluting with a solvent gradient of 25–45% $Et_2O$/ hexanes. The title compound (8.41 g, 83% for two steps) was isolated as a mixture of Δ1 and Δ2 double bond isomers.

h) Methyl (1RS,2RS,3SR)-5-Hydroxy-3-(4methoxyphenyl)-1-(3,4-methylenedioxyphenyl)indane-2-carboxylate, To a degassed solution of methyl (RS)-5-benzyloxy-3-(4-methoxyphenyl)-2-(3,4-methylenedioxyphenyl)indene-2-carboxylate (6.60 g, 13.0 mmol) in EtOAc (25 ml) and EtOH (175 ml) was added 5% palladium on activated carbon (0.6 g). The resulting suspension was shaken on a Parr hydrogenator at 60 psi $H_2$ for 20 h, at which time NMR analysis of the reaction mixture indicated that the reaction was incomplete. The catalyst was removed by filtration through a pad of Celite, and fresh 5% palladium on activated carbon (0.6 g) was added. The mixture was shaken on a Parr hydrogenator at 60 psi $H_2$ for an additional 48 h. The catalyst was removed by filtration through a pad of Celite, and the filtrate was concentrated under reduced pressure. The residue was crystallized from EtOAc/hexanes to afford the title compound (4.83 g, 89%); m.p. 187–188° C.

i) (1RS,2SR. 3SR)-5-Hydroxy-3-(4-methoxyphenyl)-1-(3,4-methylenedioxyphenyl)indane-2-carboxylic acid sodium salt. To a solution of methyl (1RS,2RS,3SR)-5-hydroxy-3-(4-methoxyphenyl)-1-(3,4-methylenedioxyphenyl)indane-2-carboxylate (150 mg, 0.36 mmol) in EtOH (4 ml) was added 10% NaOH (4 ml), and the resulting mixture was allowed to stir under an argon atmosphere overnight. Water (5 ml) was added, and the mixture was concentrated under reduced pressure. The concentrate was extracted with $Et_2O$, and the aqueous phase was acidified and extracted with EtOAc. The EtOAc extract was washed successively with H₂O and saturated aqueous NaCl and dried. The solvent was removed in vacuo. The sodium salt was prepared, and a portion of this (100 mg) was purified by reverse-phase chromatography to afford the title compound (73 mg, 48%). Trituration of this material with EtOAc provided a white crystalline solid; m.p. 198° C. (dec).

¹H NMR (MeOH-d₄): δ 7.20 (dd, 2H, J=6.8 Hz, 2.0 Hz); 6.85 (dd, 2H, J=6.8 Hz, 2.0 Hz); 6.80–6.64 (m, 5H); 6.25 (s, 1H); 5.88–5.87 (m, 2H); 4.47 (d, H, J=10 Hz); 4.43 (d, H, J=10 Hz); 3.76 (s, 3H); 3.03 (t, 1H, J=10 Hz). MS (m/e): 427 [(M+H)⁺].

EXAMPLE 12

+(1S,2R,3S)-3-(2-Carboxymethoxy-4-methoxyphenyl)-1-(3,4-methylenedioxyphenyl)-5-(prop-1-yloxy)-indane-2-carboxylic acid a) 3-Prop-1-yloxy)acetophenone. To a slurry of NaH (13.84 g, 0.58 mol) in dry DMF (50 milt) at 0° C, was added a solution of 3-hydroxyacetophenone (50 g, 0.37 mol). After stirring for 30 min. 1-iodopropane (70 mL, 0.72 mol) was added and the mixture stirred overnight at room temperature. The mixture was diluted with dry DMF (50 mL) and further NaH (2.77 g, 0.12 mol) added followed by 1-iodopropane (23 mL, 0.24 mol). After 1 h. TLC indicated that the reaction was complete and the product was cautiously quenched with 6M HCl and extracted with EtOAc. The EtOAc extract was washed successively with H₂O, 10% aqueous NaOH and then brine. After drying (MgSO₄), filtration and evaporation gave the title compound (65 g, 98%) as a light yellow oil which was used without further purification. Anal. Calc. for C₁₁H₁₄O₂: C, 74.13; H, 7.89. Found: C, 73.85; H, 7.86.

b) Methyl ³-(Prop-1-yloxy)benzoylacetate. To a suspension of NaH (12 g, 0.5 mol) in dry dimethyl carbonate (50 mL) was added slowly a solution of ³-(Prop-1-yloxy) acetophenone (65 g, 0.37 mol) in dry dimethyl carbonate (100 mL). During the addition the exothermicity of the reaction caused refluxing. Following the addition the mixture was stirred mechanically overnight and was then quenched cautiously with 3M HCl and extracted with EtOAc. The EtOAc extract was washed successively with H₂O, 5% aqueous NaHCO₃, H₂O and brine. After drying (MgSO₄), filtration and evaporation gave a yellow oil (82 g, quantitative) which was used without further purification. Anal. Calc. for C₁₃H₁₆O₄: C, 66.09; H, 6.83. Found: C, 67.25; H, 6.92.

c) Methyl 3-(3,4 -methylenedioxyphenyl)-2-[3-(prop-1-yloxy)-benzoyl]propenoate. To a solution of methyl-³-(Prop-1-yloxy)benzoylacetate (10 g, 4.2 mmol) in benzene (50 mL) was added 3, 4-methylenedioxybenzaldehyde (6.36 g, 4.2 mmol) followed by piperidine (0.42 mL, 0.42 mmol) and glacial acetic acid (8 drops approx.). The mixture was refluxed for 2 h. and the volatiles removed in vacuo to give methyl (Z)-3-(3,4-methylenedioxyphenyl)-2-[3-(prop-1-yloxy)-benzoyl]propenoate (7.4 g, 48%) as an off white solid after trituration with methanol (m. p. 122–123° C.). Anal. Calc. for C₂₁ H₂₀O₆: C, 68.47; H, 5.47. Found: C, 68.81; H, 5.49.

d) Methyl-(1RS,2SR)-1-(3.-Methylenedioxyphenyl)-5-(prop 1-yloxy)-3-oxo-indane-2-carboxylate. Methyl 3-(3, 4methylenedioxyphenyl)-2-[3-(prop-1-yloxy)-benzoyl] propenoate (7.4 g, 2.0 mmol) was dissolved in trifluoroacetic acid (50 mL) at 0° C. and the mixture stirred at room temperature for 20 min. The trifluoroacetic acid was removed in vacuo to give the title compound (6.4 g, 87%) as a white solid after trituration with warm isopropanol m. p. 106–108° C. Anal. Calc. for C₂₁H₂₀O₆: C, 68.47; H, 5.47. Found: C, 68.12; H, 5.41.

e) Methyl-3-(3,4-Methylenedioxyphenyl-6-(prop-1-yloxy)-1-oxo-indene-2-carboxylate. Methyl (1RS, 2SR)-1-(3,4-methylenedioxyphenyl)-5-(prop-1-yloxy)-3-oxoindane-2-carboxylate (26.2 g, 71 mmol) was dissolved in toluene (250 mL) and DDQ (dichlorodicyano-quinone) (16.5 g, 71 mmol) was added. The mixture was heated at 80° C. for 2 h. then cooled, filtered and the solvent removed in vacuo. The product was purified by flash column chromatography on silica gel (eluant: EtOAc/hexane, 20:80) to give the title compound as an orange solid (11.3 g, 44%) m.p. 125–126° C. Anal. Calc. for C₂₁H₁₈O₆: C, 68.85; H, 4.95. Found: C, 68.45; H,4.97.

f) Methyl-(1RS)-1-hydroxy-(4-methoxy-2-methoxymethoxyphenyl)-1,3-(3,4-methylenedioxyphenyl)-6-(prop-1-yloxy)indene-2carboxylate. To dry magnesium turnings (1.7 g, 69 mmol) under an argon atmosphere was added portionwise, a solution of 4-methoxy-2-methoxymethoxybromobenzene (16.8 g, 68 mmol) in 5% THF/ether (120 mL). The resulting 4-methoxy-2-methoxymethoxyphenyl magnesium bromide was added to a solution of methyl-3-(3,4-methylenedioxyphenyl)-6(prop-1-yloxy)-1-oxoindene -2-carboxylate (18.5 g, 51 mmol) in THF (400 mL) under an argon atmosphere at 0° C. The resulting mixture was allowed to warm to room temperature and was stirred for 10 min. The mixture was partitioned between 3M HCl and EtOAc. The organic extract was washed successively with H₂O, aqueous NaHCO₃, H₂O and saturated aqueous NaCl and dried (Na₂SO₄). The solvent was removed under reduced pressure, and the residue purified by flash chromatography on silica gel (eluant: EtOAc/ hexane, 10–20%) to afford the title compound as a yellow oil (24.5 g, 91%). Anal. Calc. for C₃₀H₃₀O₉: C, 67.41; H, 5.66;. Found: C, 67.21; H. 5.66.

SEPARATION.

Separation of (+) and (−) methyl (1RS)-1-Hydroxy-1-(4-methoxy-2-methoxymethoxyphenyl)-3-(3,4-methylenedioxybenyl)-6(prop-1-yloxy)indene-2-carboxylate was done on a column of cellulose tris(3,5-dimethylphenyl carbamate) coated on silica gel (Daicel Chiralcel OD); retention time for (+) 8.8 min. $[\alpha]^{25}_D$=+87.5° (c=0.24, CH₃OH). Retention time for (−)14.5 min. $[\alpha]^{25}_D$=+ 85.9° (c=0.21, CH₃OH) HPLC data: column Chiralcel OD (DAICEL) 21.2 mm internal diameter, 250 mm length; solvent Ethanol:Hexane 60:40; flow rate 10 mL/min.; injection: 1 g of racemate; detection UV=405 nm g) (+)Methyl-(1S,2S3S)-3-(4-methoxy-2-methoxymethoxyphenyl)-1-(3,4-methylenedioxyphenyl)-5-(prop-1-yloxy)indane-2-carboxylate. A parr vessel was charged with (+) methyl (1RS)-1-hydroxy-3-(4-methoxy-2-methoxymethoxyphenyl)-(3,4-methylenedioxyphenyl)-6-(prop-1-yloxy)indene-2-carboxylate (1 g, 1.8 mmol) dissolved in a small volume of EtOAc (25 mL) and 10% palladium on activated carbon (93 mg). The resulting solution was stirred under an atmosphere of hydrogen for 120 hours and filtered. The filtrate was concentrated under reduced pressure and the product purified by column chromatography on silica gel (eluant: EtOAc/hexane, 5–10%) to give the 12(g) as a white foam (0.80 g, 83%). $[\alpha]^{25}_D$=+ 105.4° (c=0.13, CH₃OH). Anal. Calc. for C₃₀H₃₂O₈: C, 69.22; H, 6.20.

Found: C, 68.95; H, 6.11.

h) (+)Methyl-(1S,2S,3S)-3-(2-Hydroxy-4-methoxyphenyl)-1-(3,4-methylenedioxyphenyl)-5-(prop-1-yloxy)indane-2-carboxylate. To a solution of methyl-(1S,2S,3S)-3-(2-methoxymethyl-4-methoxyphenyl)-1-(3,4 methylenedioxyphenyl)-5-(prop-1-yloxy)indane-2-carboxylate (0.7 g, 1.3 mmol) in methanol (10 mL) concentrated HCl (0.1 mL) was added and it was then heated to reflux for 2 h. The solvent was then eliminated under vacuum and the residue was purified by column chromatography on silica gel (eluant: EtOAc/hexane, 10–20%) to give the 12(h) as a colorless glass (0.50 g, 78%). $[\alpha]^{25}_D$=+116.0° (c=0.18, CH30H). Anal. Calc. for $C_{28}H_{28}O_7 \cdot \frac{1}{2} H_2O$: C, 69.27; H, 6.02. Found: C, 69.59; H, 5.99.

i) (+)Methyl-(1S,2S,3S)-3-(2-Carboethoxymethoxy-4-methoxyphenyl)-1-(3,4-methylenedioxyphenyl)-5-(prop-1-yloxy)indane-2-carboxylate. A solution of methyl-(1S,2S,3S)-3-(2-hydroxy-4-methoxyphenyl)-1-(3,4-methylenedioxyphenyl)-5-(pro 1-yloxy)indane-2-carboxylate (0.1 g, 0.2 mmol) in dry DMF (2 mL) was added to NaH (6 mg, 0.24 mmol) in a small volume of dry DMF at 0° C. The mixture was stirred at 0° C. for 15 min. and ethyl bromoacetate was then added (42 mg, 0.25 mmol). The resulting mixture was stirred at 0° C. for 1 h. The reaction was then quenched with dilute HCl and extracted with EtOAc. The EtOAc extract was washed with water then brine, dried (MgSO₄), filtered and evaporated. The product was purified by column chromatography on silica gel (eluant: EtOAc/hexane, 10–15%) to give the 12(i) as a glassy solid (82 mg, 68%).$[\alpha]^{25}_D$=+116.0° (c=0.45, CH₃OH). Anal. Calc. for $C_{32}H_{34}O_9$; C, 68.32; H, 6.09. Found: C, 67.98; H, 6.09.

j) (+) (1S,2R,3S)-3-(2-Carboxymethoxy-4methoxyphenyl)-1-(3,4-methylenedioxyphenyl)-5-(pro1-yloxy)indane-2-carboxylic acid. To a solution of methyl-(1S,2S,3S)-3-(2-carboethoxymethoxy-4methoxyphenyl)-1-(3,4-methylenedioxyphenyl)-5-(prop-I-yloxy)indane-2-carboxylate (20 mg, 0.04 mmol) in dioxane (1 mL) was added 3 M NaOH solution (0.3 mL, 1 mmol). The reaction mixture was heated to reflux for 4 h and after cooling the solvent was eliminated in vacuo dissolved in water and acidified with 3N HCl. The resulting precipitate was collected by filtration and dried to give a white solid (15 mg, 81%); m.p. 99–102 $[\alpha]^{25}_D$=+38.1° (c=0.22, CH₃OH). Anal. Calc. for $C_{29}H_{28}O_9$: C, 66.92; H, 5.42.

Found C, 67.37; H, 5.32.

EXAMPLE 12A

Preparation of 1-Bromo-methoxy-2-methoxymethoxybenzene.

a) 1-Bromo-2-hydroxy-4-methoxybenzene. 3-Bromo-2-hydroxy-6-methoxybenzoic acid [T. de Paulis et. al., *J. Med. Chem.* (1985), 28, 1263–1269] (5 g, 0.02 mol) was heated in quinoline (200 mL) at 160° C. for 1 h. On cooling, the product was partitioned between Et₂O and 3M HCl. The organic extract was washed with water and brine then dried (MgSO₄), filtered and evaporated to give the title compound which was recrystallized from 5% ethyl acetate/hexane (4 g, 97%); m.p. 40–42° C. Anal. Calc. for $C_7H_7 BrO_2$: C, 41.41; H, 3,48.

Found C, 41.39; H, 3.37.

b) 1-Bromo-4-methoxy-2-methoxymethoxybenzene. To a suspension of NaH (2.5 g, 0.06 mol) in dry DMF (100 mL) at 0° C. was added solution of 1-bromo-2-hydroxy-4-methoxybenzene (10.6 g, 0.05 mol). After stirring at 0° C. for 30 min. bromomethyl methyl ether (7.8 g, 0.06 mmol) were dropwise added. The mixture was warmed to room temperature over 20 min. and then stirred for 2 h, it was then quenched cautiously by the addition of cold dilute HCl and extracted with EtOAc. The EtOAc extract was washed successively with; H₂O, 5% aqueous NaHCO₃, H₂O and finally brine. After drying (MgSO₄) filtration and evaporation gave liquids. The product was purified by distillation (85° C., 0.2 mm Hg) to give the title compound as a colorless oil (13.7 g, 97%).

¹H NMR (CDCl₃) δ 7.40 (d, 1 H, J=8.9 Hz), 6.75 (d, 1 H, J=2.8 Hz), 6.46 (dd, 1 H, J=8.9, 2.8 Hz), 5.23 (s, 2 H), 3. 77 (s, 3 H), 3.52 (s, 3 H).

EXAMPLE 13

(1RS,2RS,3RS)-3-[2-(3-Hydroxyprop-1-yloxy)-4-methoxyphenyl-1-(3,4methylenedioxyphenyl)-5-(prop-1-yloxy)-indane-2-carboxylic acid, Methyl (1RS,2RS,3RS)-3-(2-Hydroxy-4-methoxyphenyl)-1-(3,4-methylenedioxyphenyl)-5-(prop-1-yloxy)-indane-2-carboxylate (0.14 g, 0.29 mmol) in dry DMF (1 ml) was added to NaH (9 mg, 0.38 mmol) in a small volume of dry DMF. The mixture was stirred at ambient temperature for 20 min then 3-bromopropan-1-ol (37 μl, 0.41 mmol) was added. After stirring for 1 h. the product was partitioned between 3M aqueous HCl and ethyl acetate. The organic layer was washed with water then brine, then dried (MgSO₄ anhyd.) filtered and evaporated to give an oil. The product was purified by column chromatography to provide methyl (1RS,2RS,3RS)-3-[2-(3-Hydroxyprop-1-yloxy)-4-methoxyphenyl]-1-(3,4-methylenedioxyphenyl)-5-(prop-1-yloxy)indane-2-carboxylate (0.1 g, 65%)(¹H-NMR indicated some epimerization had occurred at C-2). This material was used without further purification . Methyl (1RS, 2RS, 3RS)-3-[2-(3-Hydroxyprop-1-yloxy)4-metboxyphenyl]-1-(3,4methylenedioxyphenyl)-5-(prop-1-yloxy)indane-2-carboxylate (0.04 g, 0.075 mmol) was dissolved in methanol (2ml) and aqueous potassium hydroxide added (2M, 0.22 ml, 0.44 mmol). The mixture was stirred under reflux overnight then cooled, diluted with water, acidified with 3M aqueous hydrochloric acid and extracted with ethyl acetate. The organic extract was washed with water and brine, dried (MgSO₄ anhydrous), filtered and evaporated to give an oil. The product was purified by chromatography on silica-gel (eluant: ethyl acetate/hexane/3% acetic acid) to give 12 mg of free acid which was converted to its dicyclohexylamine salt m.p. 110–112° C.

EXAMPLE 14

(1RS,2SR, 3RS)-3-[2-(1-Carboxyeth-2-yloxy)-4-methoxyphenyl]-1-(3,4-methylenedioxypbenyl)-5-(prop-1-yloxy)-indane-2-carboxylic acid, bis-dicyclohexylamine salt (1RS,2SR,3RS)3-[2-(3-Hydroxyprop-1-yloxy)-4-methoxyphenyl]-1-(3,4-methylenedioxyphenyl)-5-(prop-1-yloxy)indane-2-carboxylic acid (0.07 g, 0.13 mmol) was dissolved in dry dichloromethane (0.5 ml) and Dess-Martin periodinane (0.07 g, 0.17 mmol) added in dry dichloromethane (1 ml). After 2 h. the product was partitioned between ether and saturated aqueous sodium carbonate solution containing sodium thiosulfate. The ether extract was washed with water then brine, dried (MgSO₄ anhydrous), filtered and evaporated to give an oil which was used without purification. The crude product was dissolved in t-butanol (5 ml) and to this was added a solution of sodium chlorite (18 mg, 0.2 mmol) and sulfamic acid (21 mg, 0.22 mmol) in water (1.5 ml). After 1 h. stirring at ambient temperature the product was extracted into ethyl acetate. The organic layer was washed with water then brine then dried (MgSO$_4$ anhyd.) filtered and evaporated to give an oil. The product was purified by column chromatography on silica-gel (eluant: ethyl acetate/hexane/3% acetic acid) to give 12mg of free acid which was converted to its bis-dicyclohexylamine salt.

m.p. 160–162° C.

MS (exact mass) M$^+$·: 534.1879 (free di-acid)

($\Delta$=+1.1 mDa for C$_{30}$H$_{30}$O$_9$)

By the methods given above, the following compounds were made:

EXAMPLE 15

(1RS)-1-(4-Methoxyphenyl)-3-phenylindene-2-carboxylic acid m.p. 191–193° C.

Anal. Calcd. for C$_{23}$H$_{18}$O$_3$: C, 80.68; H, 5.30.

Found: C, 80.54; H, 5.33.

EXAMPLE 16

(Trans, Trans)-1,3-Diphenylindane-2-carboxylic acid m.p. 164–165° C.

MS (m/e): 332 [(M+NH$_4$)$^+$].

EXAMPLE 17

(1RS, 2RS, 3SR)-1-(4-Hydroxyphenyl)3-phenylindane-2-carboxylic acid MS (m/e): 331 ((M+H)$^+$].

EXAMPLE 18

(1RS, 2RS, 3SR)-1-(4-Carboxyphenyl)-3-phenylindane-2-carboxylic acid MS (m/e): 359 [(M+H)$^+$].

EXAMPLE 19

(1RS, 2RS, 3SR)-1-(3-Methoxyphenyl)-3-pbenylindane-2-carboxylic acid MS (m/e): 362 [(M+NH$_4$)$^+$].

EXAMPLE 20

1RS, 2RS, 3SR)-1-(4-Ethylphenyl)-3-phenylindane-2-carboxylic acid m.p. 163–164° C.

MS (m/e): 360 [(M+N$_4$)$^+$].

Anal. Calcd. for C$_{24}$H$_{22}$O$_2$: C, 84.18; H, 6.48.

Found: C, 84.24; H, 6.73.

EXAMPLE 21

(1RS,3RS)-1,3-Dipbenylindane-2-carboxylic acid m.p. 220–222° C. (dec).(disodium salt).

EXAMPLE 22

(1RS,2RS,3SR)-]-(4But-4-yloxyphenyl)-3-(4-methoxyphenyl)indane-2-carboxylic acid $^1$H NMR (CDCl$_3$): δ 7.26–7.17 (m, 6H); 6.93–6.87 (m,6H); 4.62 (d, 2H, J=10.1 Hz); 3.96 (t, 2H,J=6.5 Hz); 3.81 (s, 3H); 3.29 (t, 1H,J=10.1 Hz); 1.80–1.73 (m, 2H); 1.54–1.45 (m, 2H); 0.98 (t, 31, J=7.3 Hz).

EXAMPLE 23

(1RS,2SR,3SR)-1-(4-Acetamidophenyl)-3-(4-methoxyphenyl)indane-2-carboxylic acid m.p. 231–232° C.

MS (m/e, rel. int.): 803 [(2M+1)$^+$, 100].

Ana. Calcd. for C$_{25}$H$_{23}$NO$_4$·½ H$_2$O: C, 73.12; H. 5.85; N, 3.41. Found: C, 72.92; H, 5.61; N, 3.24.

EXAMPLE 24

(1RS, 2SR, 3SR)-1-(4-Aminophenyl)-3-(4-methoxyphenyl)indane-2-carboxylic acid, dicyclohexylamine salt m.p. 187–190° C.

MS (m/e, rel. int.): 1076.2 [(2M+1)$^+$, 25].

EXAMPLE 25

(1RS, 2SR, 3SR)-1-(4-Hydroxyphenyl)-3-(3,4-methylenedioxyphenyl)indane-2-carboxylic acid m.p. 94–96° C.

MS (m/e): 392.4 [(M+NH$_4$)$^+$].

EXAMPLE 26

(1RS, 2RS, 3SR)-1-(3,4-Dimethoxyphenyl)-3-(4-methoxyphenyl)indane-2-carboxylic acid m.p. 126–128° C.

MS (m/e, rel. int.): 807 [(2M+1)$^+$, 35]; 403 [(M—H)$^-$, 100].

Anal. Calcd. for C$_{25}$H$_{24}$O$_5$: C, 74.24; H, 5.98. Found: C, 74.10; H, 5.99.

EXAMPLE 27

(1RS,2RS,3SR)-1-(3A-Methylenedioxyphenyl)-3-(4-methylthiophenyl)indane-2-carboxylic acid MS (exact mass): (M)$^+$=404.1074 ($\Delta$=+0.8 mDa for C$_{24}$H$_{20}$O$_4$S).

EXAMPLE 28

(1RS,2SR, 3SR)-5-Methoxy-3-(4methoxyphenyl)-1-(3,4-methylenedioxyphenyl)indane-2-carboxylic acid m.p. 129–131° C.

MS (m/e): 441.2 [(M+Na)$^+$].

EXAMPLE 29

(1RS,2SR, 3SR)-3-Bis(3,4-methylenedioxyphenyl)-5-hydroxyindane-2-carboxylic acid MS (m/e): 436.2 [(M+NH$_4$)$^+$].

EXAMPLE 30

(1RS,2SR, 3SR)-3-(2-Carboxymethoxy-4-methoxyphenyl)-1-(2-methoxy-4,5-methylenedioxypbenyl)-5-(prop-1-yloxy)-indane-2-carboxylic acid Methyl (1RS, 2RS, 3SR)-5-Hydroxy-3-(4-methoxy-2-methoxymethoxyphenyl)-1-(2-methoxy-4,5-methylenedioxyphenyl)indane-2-carboxylic acid was prepared in 23% overall yield from methyl 2-(3-benzyloxy) benzoylacetate according to the method of example 11. The 5-hydroxyl moiety was then propylated according to the method given in example 12 and this crude material treated according to the method of example 70 to remove the methoxymethyl group in 55% yield. The title compound was then obtained following the procedure given for example 12 in 42% yield. m.p. 188–190° C. Anal. Calc. for $C_{30}H_{30}O_{10}$: C, 65.45; H, 5.49. Found: C, 65.38; H, 5.49

EXAMPLE 31

(1RS,2SR, 3RS)-3-&4-methoxy-2-methoxymethoxyphenyl)-1-(3,4-methylenedioxyphenyl)-5-(prop-1-yloxy)indane-2-carboxylic acid m.p. 161–163° C.

EXAMPLE 32

(1RS,2SR, 3RS)-3-(Hydroxy-4-methoxyphenyl)-1-(3,4-methylenedioxyphenyl)-5-(prop-1-yloxy)indane-2-carboxylic acid (exact mass) $M^+$: 462.1678 ($\Delta$=−0.4 mDa for $C_{27}H_{26}O_7$)

EXAMPLE 33

(1RS,2SR, 3SR)-3-(2-Carboxymethoxy-4-methoxyphenyl)-1-[2-(prop-1-yloxy-4,5-methylenedioxyphenyl]-5-(prop-1-yloxy)indane-2-carboxylic acid Anal Calc. for $C_{32}H_{34}O_{10}\cdot 0.5\ H_2O$: C, 65.41; H, 6.00. Found: C, 65.27; H, 5.99, m.p. 196–197° C.

EXAMPLE 34

(1RS,2SR,3RS)-1-(2-Carboxymethoxy-4,5-methylenedioxyphenyl)-3-(4-methoxyphenyl)-5-(prop-1-yloxy)indane-2-carboxylic acid MS (DCI $NH_3$) m/e: 538.2 $(M+NH_3)^+$, 520.2 $(M+H)^+$ (exact mass) $M^+$: 520.1733 ($\Delta$=0.0 mDa for $C_{29}H_{28}O_9$)

EXAMPLE 35

(1RS,2SR,3RS)-1-(3,4-Methylenedioxyphenyl)-3-[2-(prop-1-yloxy)phenyl]-5-(prop-1-yloxy)indane-2-carboxylic acid m.p. 179–180° C.

MS(DCI $CH_4$) m/e: 503.2 $(M+C_2H_5)^+$, 474.1 $(M+H)^+$ (exact mass) $M^+$: 474.2034 ($\Delta$=+0.8 mDa for $C_{29}H_{30}O_6$)

EXAMPLE 36

(1RS,2SR, 3RS)-3-(2-Hydroxyphenyl)-1-(3,4-methylenedioxyphenyl)-5-(prop-1-yloxy)indane-2-carboxylic acid m.p. 97–98° C.

M (exact mass) $M^+$: 432.1568 ($\Delta$=+0.5 mDa for $C_{26}H_{24}O_6$)

EXAMPLE 37

(1RS,2SR, 3RS)-3-(2-Carboxymethoxyphenyl)-1-(3,4-methylenedioxyphenyl)-5-(prop-1-yloxy)indane-2-carboxylic acid m.p. 169–170° C.

Anal. Calc. for $C_{28}H_{26}O_8\cdot 0.25\ H_2O$: C, 67.94; H. 5.40. Found: C, 67.75; H, 5.37.

EXAMPLE 38

(1RS,2SR, 3RS)-3-(2-Benzyloxy-4-methoxyphenyl)-1-(3,4-methylenedioxyphenyl)-5-(prop-1-yloxy)indane-2-carboxylic acid MS (exact mass) $M^+$: 552.2149 ($\Delta$=−0.1 mDa for $C_{34}H_{32}O_7$)

EXAMPLE 39

(1RS,2SR, 3RS)-3-[2-(2-Hydroxyeth-1-yloxy)-methoxyphenyl]-1-(3,4-methylenedioxyphenyl)-5-prop-1-yloxy)indane-2-carboxylic acid, dicycohexylamine salt m.p. 182–184° C.

Anal. Calc. for $C_{41}H_{53}NO_8$: C, 71.59; H, 7.77; N,2.04. Found: C, 71.67; H,7.66; N,2.42.

EXAMPLE 39A (+) (1S, 2R, 3S)-3-2-(2-Hydroxyeth-1-yloxy)-4-methoxyphenyl]-1-(3,4-methylenedioxyphenyl)-5-propoxyindane-2-carboxylic acid a) Benzyloxyethylbromide A mixture of benzyl bromide (103 g, 0.60 moles) and tetrathylammonium iodide (3.1 g, 0.012 moles) under argon was heated to 145° C. Ethylene carbonate (84.5 g, 0.96 moles) was added over 0.75 hr., and the reaction mixture stirred at 145–160° C. for 24 hrs. The mixture was cooled, diluted with 250 ml of deionized water and extracted with 2×200 ml of methylene chloride. The organic extracts were washed with brine, dried over $MgSO_4$, and concentrated in vacuo. Distillation gave 90 g (70%) of product as a light yellow liquid (b.p. 80–85° C., 0.5 mm).

b) 1-Bromo-2-(2-benzyloxyeth-1-yloxy)4-methoxybenzene

A mixture of 1-bromo-2-hydroxy-4-methoxy benzene (68.3 g, 0.336 moles), anhydrous potassium carbonate (51.2 g 0.37 moles) and 0.5L of N,N-dimethylformamide was heated to 65° C. Benzyloxyethylbromide (76.0 g, 0.353 moles) was added dropwise over 0.5 hr. After stirring for 1.5 hr. at 65° C., the reaction mixture was cooled and filtered. The filtrate was diluted with 1L of deionized water, and extracted with 3×0.5L ethyl acetate. The organic extracts were washed with brine, dried over $MgSO_4$, and concentrated in vacuo. Distillation gave 93 g (83%) of product as a yellow liquid (b.p. 170–175° C., 0.5mm).

c) Methyl(1SR)-1-hydroxy-3-(2-benzyloxyetb-1-yloxy)-4-methoxyphenyl]-1-(3,4-methylene dioxyphenyl)-5-propoxyindene-2-carboxylate A solution of 1-bromo-2-(2-benzyloxyeth-1-yloxy)-4-methoxybenzene (161 g, 0.478 moles) and 1.6L of tetrahydrofuran @−70° C. under argon was treated with n-butyl lithium (190 mL, 2.5 m, 0.478 moles), followed by magnesium bromide etherate (132 g, 0.512 moles). After stirring for 0.5 hr., a solution of methyl-3-(3,4-methylenedioxyphenyl)-5-propoxy-1-oxo-indene-2-carboxylate (117 g, 0.32 moles) in 1L of tetrahydrofuran was added over 0.5 hr. The reaction mixture was stirred for 1 hr. at −70° C., and quenched by addition of aqueous ammonium chloride. The mixture was extracted with 3×1L of methyl t-butylether. The organic extracts were washed with brine, dried over $MgSO_4$, and concentrated in vacuo to give 240 g of crude product. Chromatography on 1.5 Kg silica gel using a hexane: methylene chloride: ethyl acetate gradient gave 175 g (88%) of light orange oil.

d) Methyl (1SR, 2SR, 3SR)-3-[2-(2-hydroxyeth-1-yloxy)-4-methoxyphenyl]-1-(3,4-methylenedioxy phenyl)-5-propoxyindane-2-carboxylate A mixture of methyl (1SR)-1-hydroxy-3-[2-(2-benzyloxyeth-1-yloxy)-4-methoxyphenyl]-1-(3, 4methylenedioxy phenyl)5-propoxyindene-2-carboxylate (88 g, 0.141 moles) 10% palladium on carbon (21 g), 0.65 L of absolute ethanol and 0.65 L of ethylacetate was hydrogenated at 50 psi, 55° C. for 48 hrs. The catalyst was filtered off, and the filtrate concentrated in vacuo to give an amorphous glass. Crystallization from 350 mL of absolute ethanol gave 59.5 g (81%) of white solid;

m.p. 165–168° C.

Chiral Resolution

Separation of (+) and (−) methyl (1SR, 2SR, 3SR)-3-[2-(2-hydroxyeth-1-yloxy)-4-methoxyphenyl]-1-(3,4methylenedioxyphenyl)-5-propoxyindane-2-carboxylate was accomplished using an amylose tris (3,5-dimethylphenylcarbamate) coated on silica gel (Daicel Chiralpak AD). The mobile phase consisted of 50:40:10 - hexane: isopropanol: chloroform. The retention times of the enantiomers were 4.7 min (+isomer), and 9.2 min (−isomer), using a 4.6×250 mm column at 1.0 ml/min.

e) (+) (1S, 2R, 3S3-[2-(2-Hydroxyeth-1-yloxy)-4methoxyhenyl]-1-(3,4-methylenedioxyphenyl)-5-propoxyyindane-2carboxylic acid To a solution of (+) methyl (1S, 2S, 3S)-3-[2-(2-hydroxyeth-1-yloxy)-4-methoxyphenyl]-1-(3,4-methylenedioxyphenyl)-5-propoxyindane-2-carboxylate (69.3 g, 0.133 moles) in 1.4 L of methanol and 0.14 L of deionized water was added 50% aqueous sodium hydroxide (0.059 L, 0.74 moles). The reaction mixture was refluxed for 16 hrs. After concentrating the mixture in vacuo, the slurry was diluted with 1 L of deionized water, and acidified to pH 2 with 3 N HCl. The mixture was extracted with 3×500 mL of methyl-t-butyl ether. The organic extracts were combined, washed with brine, dried of $MgSO_4$, and concentrated in vacuo. The resulting oil was crystallized from 400 mL of isopropanol to give 40.7 g (60%) of white solid; m.p. 119–122° C; $[\alpha]_D^{24°\ C.}$ =+60.4° (C=0.5, $CH_3OH$).

Formation of the hemiethylenediamine salt gave a white crystalline solid; m.p. 177–179° C.; $[\alpha]_D^{24°\ C.}$=+70.0° (C=0.5, $CH_3OH$).

EXAMPLE 40 h(1RS,2SR,3RS)-3-(2-Ethoxy-4-methoxyphenyl)-1-(3,4-methylenedioxyphenyl)-5-(prop-1-yloxy)indane-2-carboxylic acid Anal. Calc. for $C_{29}H_{30}O_7$: C, 71.01; H, 6.16; Found: C, 70.71; H, 6.01.

EXAMPLE 41

(1RS,2SR, 3RS)-3-[4Methoxy-2-(prop-1-yloxy)phenyl]-1-(3,4-methylenedioxypbenyl)-5-(prop-1-yloxy)indane-2-carboxylic acid Anal. Calc. for $C_{30}H_{32}O_7$: C, 71.41; H, 6.39; Found: C, 71.43; H, 6.31.

EXAMPLE 42

(1RS,2SR, 3RS)-3-[4-Methoxy-2-(prop-2-yloxy)phenyl]-1-(3,4-methylenedioxyphenyl)-5-(prop-1-yloxy)indane-2-carboxylic acid m.p. 75–79° C.

EXAMPLE 43

(1RS,2SR, 3RS)-3-[4Methoxy-2-(2-methylprop-1-yloxy)phenyl]-1-(3,4-methylenedioxyphenyl)-5-(prop-1-yloxy)indane-2-carboxylic acid m.p. 85–89° C.

EXAMPLE 44

(1RS, 2SR, 3RS)-3)-[4-Methoxy-2-(3-methylbut-1-yloxy)phenyl]-1-(3,4-methylenedioxyphenyl)-5-(prop-1-yloxy)indane-2-carboxylic acid. dicylohexylamine salt m.p. 150–155° C.

EXAMPLE 45

(1RS,2SR, 3RS)3-[4-Methoxy-2-(3-pyridylmethoxy)phenyl]-1-(3,4-methylenedioxyphenyl)-5-(=-1-yloxy)indane-2-carboxylic acid.

Anal. Calc. for $C_{33}H_{31}N_7.0.5H_2O$: C, 71.02; H, 5.78; N, 2.51; Found: C, 71.02; H, 5.53; H, 2.30.

EXAMPLE 46

(1RS,2SR, 3RS)-3-[4-Methoxy-2-(4-pyridylmethoxy)phenyl]-1-(3,4-methylenedioxyphenyl-5-(prop-1-yloxy)indane-2-carboxylic acid.

Anal. Calc. for $C_{33}H_{31}NO_7.0.5H_2O$: C, 71.02; H, 5.78; N, 2.51; Found: C, 70.89; H, 5.59; H, 2.37.

EXAMPLE 47

(1RS,2SR, 3RS)-3-[4-Methoxy-2-(2-pyridylmetboxy)phenyl]-1-(3,4-methylenedioxyphenyl)-5-(prop-1-yloxy)indane-2-carboxylic acid m.p. 153–155° C.

EXAMPLE 48

(1RS,2SR,3RS)-3-[2-(Hept-1-yloxy)-4-methoxyphenyl]-1-(3,4-methylenedioxyphenyl)-5-(prop-1-yloxy)indane-2-carboxylic acid m.p. 70–73° C.

EXAMPLE 49

(1RS,2SR, 3RS)-3-[4-Methoxy-2-(5-tetrazolylmetboxy)phenyl]-1-(3,4-methylenedioxyphenyl)-5-(prop-1-yloxy)indane-2-carboxylic acid, m.p. 102–105° C.

EXAMPLE 50

(1RS,2SR,3RS)-3-(2-Cyanomethoxy-4-methoxyphenyl)-1-(3,4-methylenedioxyphenyI-5-(prop-1-yloxy)indane-2-carboxylic acid m.p. 199–201° C.

EXAMPLE 51

(1RS,2SR,3RS)-3-(2-Carboxamidomethoxy-4-methoxyphenyl)-1-(3,4-methylenedioxyphenyl)-5-(prop-1-yloxy)indane-2-carboxylic acid Anal. Calc. for $C_{29}H_{29}NO_8.0.5C_4H_8O$: C, 67.02; H, 5.99; N, 2.52; Found: C, 67.76; H, 5.96; H, 2.56.

EXAMPLE 52

(1RS,2SR, 3 SR)-5-Acetamido-1,3-bis(3,4-methylenedioxyphenyl)indane-2-carboxylic acid.

MS m/e: 460 [(M+H)$^+$].

EXAMPLE 53

(1RS,2SR, 3SR)-5-Amino-1,3-bis(3,4-methylenedioxyphenyl)indane-2-carboxylate, dicyclohexylamine salt, MS m/e: 418 [(M+H)$^+$].

EXAMPLE 54

(1RS,2SR,3RS)-3-[2-(3-Carboxyphenyl)-4-methoxyphenyl]-1-(3,4-methylenedioxyphenyl)-5-(prop-1-yloxy)indane-2-carboxylic acid a) Ethyl 3-[tri-(but-1-yl)stannyl)benzoate Ethyl 3-bromobenzoate (2.0 g, 8.7 mmol), hexabutyl-distannane (5.51 ml, 10.9 mmol), tetrakis(triphenylphosphine)palladium(O) (0.08 g, 0.07 mmol) and palladium (II) acetate (0.19 g, 0.85 mmol) were mixed in dry toluene (25 ml) and refluxed for 72 h under argon. The solvent was removed in vacuo and the residue purified by column chromatography on silica gel (eluant:hexane). The title compound was obtained as a colorless oil (1.1 g, 30%).

b) Methyl (1RS,2SR,3RS)-3-[2-(3-carbomethoxphenyl)-4-methoxyphenyl]-1-(3,4methylenedioxyphenyl-5-(prop-1-yloxy)indane-2-carboxylate Methyl (1RS,2SR,3RS)-3-(4-methoxy-2-trifluoromethanesulfonyloxyphenyl)-1-(3,4methylenedioxyphenyl)-5-(prop-1-yloxy)indane-2-carboxylate (0.118 g, 0.19 mmol), lithium chloride (0.058 g, 1.37 mmol), tetrakis(tri-phenylphosphine)-palladium(0) (0.018 g, 0.016 mmol) and ethyl 3-[tri-(butyl-1-yl)stannyl]benzoate (0.253 g, 0.58 mmol) were mixed in dry dimethylformamide (5 ml) and refluxed for 24 h. The product was filtered through celite and the celite washed with ethyl acetate. The combined filtrate was evaporated in vacuo and was shown to be a mixture of two components by TLC. Purification by column chromatography on silica-gel gave a less polar fraction: methyl (1RS,2SR,3SR)-3-[2-(but-1-yl)-4-methoxyphenyl)-1-(3,4-methylenedioxyphenyl)-5-(prop-1-yloxy)indane-2-carboxylate (0.038 g) which was obtained as a colorless oil. The title compound was the more polar component (0.08 g) which while contaminated with tin residues ($^1$H-NMR) was used without further purification.

c) (1RS,2SR,3RS)-3-[2-(3-Carboxyphenyl)-4methoxyphenyl]-1-(3,4-methylenedioxyphenyl)-5-1-prop-1-yloxy)-indane-2-carboxylic acid Methyl (1RS,2SR,3RS)-3-[2-(3Carboxyphenyl)-4-methoxyphenyl]-1-(3,4-methylenedioxyphenyl)-5-(prop-1-yloxy)indane-2-carboxylate (0.08 g, crude) was dissolved in propan-2-ol (I ml) and aqueous sodium hydroxide (1M, 1 ml ,1 mmol) added. The mixture was refluxed for 12 hr. then cooled, diluted with water, acidified with 3M-aqueous hydrochloric acid and extracted with ethyl acetate (3×). The combined organic extract was purified by column chromatography on silical-gel (eluant: 30% EtOAc/hexane/5% AcOH) to give the title compound as a colorless solid (20 mg)

m.p. 257–268° C.

EXAMPLE 55

(1RS,2SR,3SR)-3-[2-(But-1-yl)4-methoxyphenyl)-1-(3,4-methylenedioxyphenyl)-5-(prop-1-yloxy)indane-2-carboxylic acid, dicyclohexylamine salt Methyl (1RS,2SR,3SR)-3-[2-(But-1-yl)-4-methoxyphenyl)-1-(3,4-methylenedioxyphenyl)-5-(prop-1-yloxy)indane-2-carboxylate (0.038 g, 0.074 mmol) was dissolved in propan-2-ol (1 ml) and aqueous sodium hydroxide (1M, 0.75 ml,0.75 mmol) added. The mixture was refluxed for 12 hr. then cooled, diluted with water, acidified with 3M-aqueous hydrochloric acid and extracted with ethyl acetate (3×). The combined organic extract was purified by column chromatography on silica-gel (eluant: 30% EtOAc/hexane then 30% EtOAc/hexane/5%AcOH). Conversion of the product to its dicyclohexylamine salt gave the title compound.

m.p. 179–182° C.

Anal. Calc. for $C_{41}H_{53}NO_8$: C, 71.59; H, 7.77; N, 2.04. Found: C, 71.67; H, 7.66; N, 2.42.

EXAMPLE 56

(1RS,2SR,3RS)-3-(4Methoxy-2-phenylphenyl)- -(3,4methylenedioxyphenyl)-5-(prop-1-yloxy)indane-2-carboxylic acid a) Methyl (1RS,2RS,3RS)-3-(4-Methoxy-2-phenylphenyl)-1-(3,4-methylenedioxyphenyl)-5-(prop-1-yloxy)indane-2-carboxylate To a slurry of anhydrous LiCl (46 mg, 1.1 mmol) and tetrakis(triphenylphosphine)-palladium(0)(24 mg, 0.02 mmol) in dry dioxane (3 mL) was added a solution of Methyl (1RS,2RS,3RS)-3-(4Methoxy-2-trifluoromethanesulfonyloxyphenyl)-1-(3,4methylenedioxyphenyl)-5-(prop-1-yloxy)indane-2-carboxylate (95 mg, 0.16 mmol) and tri(but-1-yl)stannylbenzene (319 mg, 0.87 mmol) in dioxane (1 mL). The mixture was refluxed under Argon for 17 h, cooled to room temperature, diluted with ethyl acetate (5 ml) and the resulting solution washed sequentially with brine and water. The organic layer was dried ($MgSO_4$ anhydrous), filtered through a short pad of silica gel and concentrated in vacuo to yield an oil. The product was purified by flash column chromatography (silica gel, gradient elution from hexanes to 10% ethyl acetate/hexanes) to afford the title compound as a white solid. (92 mg, 86%).

b) (1RS,2SR,3RS)-3-(4-Methoxy-2-phenylphenyl)-1-(3,4-methylenedioxyphenyl)-5-(prop-1-yloxy)indane-2-carboxylic acid To a solution of Methyl (1RS,2RS,3RS)-3-(4-Methoxy-2-phenylphenyl)-1-(3,4-methylenedioxyphenyl)-5-(prop-1-yloxy)indane-2-carboxylate (80 mg, 0.12 mmol) in dioxane (2 mL) was added 1M aqueous NaOH (0.3 mL, 0.3 mmol). The resulting mixture was heated to reflux for 48 h, then concentrated under reduced pressure. The residue was partitioned between dilute aqueous HCl and ethyl acetate. The ethyl acetate extract was washed with water and dried ($MgSO_4$ anhydrous). The solvent was removed in vacuo and the residue purified by flash column chromatography (silica gel, 20% ethyl acetate/hexane containing 5% of acetic acid) to afford the title compound (36 mg, 46%).

m.p. 199–200° C.

$^1$H NMR ($CDCl_3$) δ 7.18–7.09 (m, 6H); 6.85 (dd, 1H, J=8.6, 2.1 Hz); 6.71–6.65 (m, 6H),6.36 (b s, 1H), 5.85 (s, 2H), 4.59 (d, 1H, J=10.2 Hz); 4.31 (d, 1H, J=10.2 Hz); 3.75 (t, 2H, J=7.3 Hz); 3.73 (s, 3H); 3.14 (dd, 1H, J=10.2, 10.2 Hz); 1.68 (sextet, 2H, J=7.3 Hz); 0.93 (t, 3H, J=7.3 Hz).

MS m/e: 540 $(M+NH_4)^+$.

Anal. Calc. for $C_{33}H_{30}O_6$. ¾ $H_2O$: C, 73.93; H, 5.90. Found: C, 74.12, H, 5.80.

EXAMPLE 57

(1RS,2SR, 3SR)-3-[2-[(E)-2-Carboxyethen-1-yl]-4-methoxyphenyl]-1-(3,4-methylenedioxyphenyl)-5-(prop-1-yloxy)indane-2carboxylic acid a) Methyl (1RS,2SR, 3SR)-3-[2-[()-2-carbomethoxyethen-1-yl]-4-methoxyphenyl]-1-(3,4methylenedioxyphenyl)-5-(Drop 1-yloxy)indane-2-carboxylate.

1,3-bis(diphenylphosphino)propane (0.066 mmol), tris(dibenzylideneacetone)-dipalladium(0) (24 mg, 0.026) and bis(triphenylphosphine)palladium(II) choride (18 mg, 0.026 mmol), were dissolved in a 4:1 mixture of triethylamine/acetonitrile (5 mL) under argon. After 10 min at room temperature, a solution of methyl (1RS, 2SR, 3RS)-3-(4-methoxy-2-trifluoromethanesulfonyloxyphenyl)-1-(3,4-methylenedioxyphenyl)-5-(prop-1-yloxy)indane-2- carboxylate (160 mg, 0.26 mmol) and methyl acrylate (679 mg, 7.89 mmol) was added in the above solvent mixture (3 mL). The reaction mixture was heated to reflux under argon for 20 h, cooled to room temperature and a small aliquot analyzed by $^1$H NMR, which showed no reaction had taken place. Palladium(l) acetate (6 mg, 0.025 mmol) and methyl acrylate (679 mg, 7.89 mmol) in dry DMF (5 mL) were then added. The reaction mixture was heated to reflux overnight. On cooling the solution was filtered through a short column of silica gel and concentrated to yield an oil. The crude product was purified by flash column chromatography ( silica gel, gradient elution: 10% to 20% ethyl acetate/hexanes) to afford the title compound as a tan solid. (87 mg, 62%).

$^1$H NMR (CDCl$_3$): δ 8.17 (d, 1H, J=15.7 Hz); 7.44 (d, 1H, J=8.7 Hz), 7.11–7.07 (m, 2H); 6.90–6.70 (m, 6H), 6.42 (d, 1H, J=15.7 Hz); 5.94 (b s, 2H), 5.04 (d, 1H, J=7.5 Hz); 4.75 (d, H, J=7.6 Hz); 3.89 (t, 2H, J=6.7 Hz); 3.85 (s, 3H); 3.85 (dd, 1H, J=7.5, 7.4 Hz); 3.83 (s,3H); 2.96 (s,3H), 1.79 (sextet, 2H, J=6.7 Hz); 1.03 (t, 3H, J=6.7 Hz).

b) (1RS,2SR, 3SR)-3-[2-[(E)-2-Carboxyethen-1-yl]-4-methoxyphenyl]-1-(3,4-methylenedioxyphenyl)-5-(prop-1-yloxy)indane-2-carboxylic acid.

To a solution of methyl (1RS, 2SR, 3SR)-3-[2-[(E)-2-carbomethoxyethen-1-yl]-4-methoxyphenyl]-1-(3,4-methylenedioxyphenyl)-5-(prop-1-yloxy)indane-2-carboxylate (80 mg, 0.15 mmol) in dioxane (2 ml) was added 1 N NaOH (0.5 ml, 0.5 mmol). The resulting mixture was heated to reflux for 3 h, then cooled and concentrated under reduced pressure. The residue was partitioned between dilute aqueous HCl and ethyl acetate. The ethyl acetate extract was washed with water and dried (MgSO$_4$ anhydrous). The solvent was removed in vacuo and the title compound was obtained as a white solid (73 mg, 96%).

$^1$H NMR (CDCl$_3$): δ 8.32 (d, 1H, J=15.6 Hz); 7.24–6.55 (m, 9H); 6.29 (d, 1H, J=15.6 Hz); 5.94 (b s, 2H), 5.18 (d, 1H, J=9.9 Hz); 4.69 (d, 1H, J=9.9 Hz); 3.85 (s, 3H); 3.84 (t, 2H, J=6.9 Hz); 2.94 (dd, 1H, J=9.9, 9.9 Hz); 1.79 (sextet, 2H, J=6.9 Hz); 1.00 (t, 3H, J=6.9 Hz).

MS m/e: 517 [(M+H)$^+$].

Ana. Calc. for C$_{30}$H$_{28}$O$_8$: C, 69.76; H, 5.46. Found: C, 69.73, H, 5.26.

EXAMPLE 58

(1RS,2SR, 3SR)-3-[2-(2-Carboxyeth-1-yl-4-methoxyphenyl]-1-(3,4-methylenedioxyphenyl)-5-(prop-1-yloxy)indane-2-carboxylic acid.

To a solution of (1RS, 2SR, 3 SR)-3-[2-[(E)2-carboxyethen-1-yl]4-methoxyphenyl]-1-(3,4-methylenedioxyphenyl)-5-(prop-1-yloxy)indane-2-carboxylic acid (43 mg, 0.08 mmol) in ethanol (5 mL) was added 10% palladium on activated carbon (40 mg). The resulting suspension was stirred overnight under an atmosphere of hydrogen then filtered through a pad of celite. The filtrate was concentrated under reduced pressure to afford the title compound (35 mg, 82%) as a white solid.

$^1$H NMR (CDCl$_3$): δ 6.99 (d, 1H, J=8.6 Hz); 6.78–6.66 (m, 7H); 6.23 (b s, 1H); 5.88–5.87 (m, 2 H); 4.88 (d, 1H, J=9.7 Hz); 4.54 (d, 1H, J=9.7 Hz); 3.72 (s, 3H); 3.70 (t, 2H, J=7 Hz); 2.98–2.90 (m, 1H); 2.68–2.51 (m, 2H); 1.65 (sextet, 2H,J=7.0 Hz); 0.89 (t, 3H, J=7.0 Hz). M (exact mass) M$^+$: 518.1930 (D=+1.1 mDa for C$_{27}$H$_{26}$O$_7$)

By the methods given above in Examples 54 to 58, the following compounds were made.

EXAMPLE 59

(1RS,2SR,3RS)-3-(2-Carboxymethylthio-4-methoxyphenyl)-1-[3,4-methylenedioxyphenyl)-5-(prop-1-yloxy)indane-2-carboxylic acid m.p. 242–246° C. (dec).

(1RS,2SR, 3SR)-3-[4-Methoxy-2-[prop-2-en-1-yl)phenyl]-1-(3,4-methylenedioxyphenyl)-5-(prop-1-yloxy)indane-2-carboxylic acid m. p. 126–127° C. (exact mass) M$^+$: 486.2021 (Δ=+2.1 mDa for C$_{30}$H$_{30}$O$_6$)

EXAMPLE 61

(1RS,2SR, 3SR)-3-[4Methoxy-2-(prop-1-yl)phenyl]-1-(3,4-methylenedioxyphenyl)-5-(prop-1-yloxy)indane-2-carboxylic acid m.p. 155–156° C.

Anal. Calc. for C$_{30}$H$_{32}$O$_6$: C, 73.75; H, 6.60. Found: C, 73.45, H, 6.43.

EXAMPLE 62

(1RS,2SR, 3RS)-3-[2-Carboxy-4-methoxyphenyl]- 1-(3,4-methylenedioxyphenyl)-5-(prop-1-yloxy)indane-2-carboxylic acid.

Anal. Calc. for C$_{28}$H$_{26}$O$_8$: C, 68.56; H, 5.34. Found: C, 68.61, H, 5.58.

EXAMPLE 63

(1RS,2SR, 3 SR)-3-[2-(2-Hydroxyethyl)-4-metboxyphenyl]-1-(3,4-methylenedioxyphenyl)-5-(prop-1-yloxy)indane-2-carboxylic acid (exact mass) M$^+$: 490.1994 (Δ=+0.3 mDa for C$_{29}$H$_{30}$O$_7$)

EXAMPLE 64

(1RS,2SR, 3 SR)-3(2-Carboxymethyl-4-methoxyphenyl)-1-(3,4-methylenedioxyphenyl)-5-(prop-1-yloxy)indane-2-carboxylic acid (exact mass) M$^+$.: 504.1788 (D=–0.4 mDa for C$_{29}$H$_{28}$O$_8$)

EXAMPLE 65

(1RS,2SR, 3SR)-3-[2-(3-Hydroxyprop-1-yl)-4-metboxyphenyl]-1-(3,4-methylenedioxyphenyl)-5-(prop-1-yloxy)indane-2-carboxylic acid MS (exact mass) M$^+$.: 504.2143 (Δ=+0.5 mDa for C$_{30}$H$_{32}$O$_7$)

EXAMPLE 66

(1RS,2SR, 3 SR)-5-(4Carboxyphenyl)-1,3-bis(3,4-methylenedioxyphenyl)-1-indane-2-carboxylic acid.

m.p. 230–231° C.

EXAMPLE 67

(1RS, 2SR, 3SR)-5-(4-Benzyloxyphenyl)-1.3-bis(3,4-methylenedioxyphenyl)indane-2-carboxylic acid, m.p. 105–106° C.

EXAMPLE 68

(1RS,2SR, 3SR)-5-(14-Hydroxyphenyl)-1,3-bis(3,4-methylenedioxypbenyl)indane-2-carboxylic acid.

MS m/e: 512 [(M+NH$_4$)$^+$].

EXAMPLE 69

(trans, trans-1,3,5-tris(3,4-methylenedioxyphenyl)indane-2-carboxylic acid.

Anal. Calc. for C$_{31}$H$_{22}$O$_8$.⅝ H$_2$O: C, 69.76; H, 4.39. Found: C, 69.81, H, 4.46.

EXAMPLE 70

(1RS,3RS)-3-(2-Hydroxy-4-methoxyphenyl)-1-(3,4-methylenedioxyphenyl)-5-(prop-1-yloxy)indane.

a) (1RS,3RS)-3-[(2-Methoxymethoxy)-4-methoxyphenyl)]-1-(3,4-methylenedioxyphenyl)-5-(prop-1-yloxy)indane.

A solution of (1RS, 2SR, 3RS)-3-[2-(methoxymethoxy)-4-methoxyphenyl]-1-(3,4-methylenedioxyphenyl)-5-(prop-1-yloxy)indane-2-carboxylic acid (0.2 g, 0.39 mmol) in dichloromethane (4 ml) and pyridine (28 µl, 1.6 mmol) was cooled to 0° C. under argon. To this solution was added thionyl chloride (60 µl, 0.8 mmol). The mixture was allowed to warm to ambient temperature over 20 min. and the volatiles removed in vacuo. The residue was redissolved in toluene and evaporated in vacuo (twice). The residue was dissolved in dichloromethane (4 ml) and triethylamine (250 µl) added. To this solution at room temperature under argon was added 2-mercaptopyridine-N-oxide (120 mg, 0.8 mmol) dissolved in dichloromethane (1 ml). After stirring for 20 min at room temperature t-butylthiol (450 µl, 4 mmol) was added and the mixture irradiated for 20 min (150 watt spotlight). The volatiles were removed in vacuo and the product partitioned between ethyl acetate and 3M-aq. HCl. The organic extract was washed with water, sat aq. $NaHCO_3$ solution and finally brine. After drying ($MgSO_4$ anhydrous), the product was filtered and evaporated Purification by column chromatography gave the title compound (0.075 g, 41%).

$^1$H NMR ($CDCl_3$): δ 7.13 (d, 1H, J=8.5 Hz); 6.83 (d, 1H, J=8.3 Hz), 6.79–6.69 (m, 5H), 6.54 (dd, 1H, J=8.5, 2.5 Hz), 6.51 (br s, 1H), 5.92 (br, s, 2H) 5.18 (d, 1H, J=6.7 Hz, ),5.15 (d, 1H, J=6.7 Hz), 4.66 (dd, J=10.5, 7.6 Hz, 1H, J=6.7 Hz), 4.22 (dd, 1H, J=10.5, 7.4 Hz), 3.81 (m, 2H), 3.80 (s, 3H), 3,43 (s, 3H), 2.90–2.83 (m, 1H), 2.06–1.98 (m, 1H), 1.73 (sextet, 1H, J=7.1 Hz), 0.92 (t, 3H, J=7.1 Hz).

b) (1RS,3RS)-3-(2-Hydroxy-4methoxyphenyl)-1-(3,4-methylenedioxybenyl)-5-(prop-1-yloxy)indane To a solution of (1RS,3RS)-3-((2-methoxymethoxy)-4-methoxyphenyl)]-1-(3,4-methylenedioxyphenyl)-5-(prop 1-yloxy)indane (0.075 g, 0.16 mmol) in methanol (5 ml) was added 4-5 drops of 6M-HCl and the mixture refluxed for 1.5 h under argon. The solvent was removed in vacuo and the product partitioned between EtOAc and water. The organic extract was washed with water then sat. aq. $NaHCO_3$ solution and finally brine. After drying ($MgSO_4$ anhydrous) filtration and evaporation gave the title compound (0.064 g, 94%).

$^1$H NMR ($CDCl_3$): δ 7.11 (d, 1H, J=8.4 Hz), 6.87 (d, 1H, J=7.8 Hz), 6.77–6.74 (4 H, m), 6.61 (br s, 1H), 6.50 (dd, 1H, J=8.4, 2.5 Hz), 6.42 (d, 1H, J=2.5 Hz), 5.94 (d, 1H J=1.2 Hz), 5.93 (d, 1H, J=1.2 Hz), 4.74 (s, 1H), 4.43 (dd, 1H, J=10.4, 7.6 Hz), 4.20 (dd, 1H, J=10.7, 7.3 Hz), 3.82 (t, 2H, J=6.7 Hz), 3.79 (s, 3H), 2.89–2.82 (m, 1H), 2.15–2.08 (m, 1H), 1.77–1.71 (sextet, 2H, J=7.2 Hz), 0.99 (t, 3H, J=2.5 Hz).

MS (exact mass) M+Found: 418.1782 (Δ=−0.2 mDa for $C_{26}H_{26}O_5$).

EXAMPLE 71

(1RS,2RS)3-(2-Carboxymethoxy-4-methoxyphenyl)-1-(3,4-methylenedioxyphenyl)-5-(prop-1-yloxy)indane To a slurry of sodium hydride (5 mg, 0.21 mmol) in dimethylformamide (0.5 ml) was added (1RS,3RS)-3-(2-hydroxy-4-methoxyphenyl)-1-(3,4-methylenedioxyphenyl)-5-(prop-1-yloxy)indane (0.058 g, 0.14 mmol) at ice-bath temperature under argon. After stirring for 15 min, ethyl bromoacetate (50 µl, 0.2 mmol) was added and the solution stirred for 1 h at room temperature. The product was partitioned between ethyl acetate and 3M aq HCl. The organic extract was washed with water, sat. aq. $NaHCO_3$ solution and finally brine. After drying ($MgSO_4$ anhydrous) filtration and evaporation followed by chromatography gave (1RS,3RS)-3-(2-carboethoxymethoxy-4methoxyphenyl)-1-(3,4-methylenedioxyphenyl)-5-(prop-1-yloxy)indane (0.041 g). The product was dissolved in hot ethanol (10 ml) and 1 M aq. NaOH added (1 ml) The mixture was refluxed for 1 h then cooled, acidified with 6M-aqueous HCl and extracted with ethyl acetate. After evaporation the residue was crystallized from ethyl acetate/hexane to give the title compound (0.035 g, 93%). m.p. 177–178° C.

$^1$H NMR ($CDCl_3$): δ 7.18 (d, 1H, J=8.5 Hz), 6.87 (d, 1H, J=8.4 Hz), 6.88–6.71 (4 H, m), 6.56 (dd, 1H, J=8.4, 2.3 Hz), 6.53 (br. s, 1H), 6.41 (d, 1H, J=2.3 Hz), 5.91 (br. s, 2H), 4.68–4.60 (m, 3H), 4.61 (dd, 1H, J=10.7, 7.2 Hz), 3.83–3.80 (m, 2H), 3.81 (s, 3H), 2.86 (dt, 1H, J=12.4, 7.2 Hz), 2.10–1.98 (m, 1H), 1.73 (sextet, 2H, J=7.2 Hz), 0.98 (t, 3H, J=7.4 Hz).

MS (exact mass) M+=476.1829 (Δ=+0.6 mDa for $C_{28}H_{28}O_7$).

EXAMPLES 72–120

The following compounds were prepared by the procedures given above. (1RS, 2SR, 3SR)-1-(4-Methoxyphenyl)-3-(3,4,5-trimethoxyphenyl)indane-2-carboxylic acid, m.p. 197–198° C.;

(1RS, 2SR, 3SR)1-(4-Ethoxyphenyl)-3-(3,4-methylenedioxyphenyl)indane-2-carboxylic acid, m.p. 169–170° C.;

(1RS, 2SR, 3SR)-5-Carboxy-1,3-bis(3,4-methylenedioxyphenyl)indane-2-carboxylic acid, m.p. 112–115° C.;

(1RS, 2SR, 3SR)-3-(4-Methoxyphenyl)-1-(3,4methylenedioxyphenyl)-5-(prop-2-en-1-yloxy)indane-2-carboxylic acid. Anal. Calc. for $C_{27}H_{24}O_6 \cdot \frac{5}{8} H_2O$: C, 71.16; H, 5.58. Found: C, 71.31; H, 5.33;

(1RS, 2SR, 3RS)-3-(2,4-Dimethoxyphenyl)-5-hydroxy-1-(3,4-methylenedioxyphenyl)indane-2-carboxylic acid, m.p. 110–113° C.;

(1RS, 2SR, 3SR)-3-[5-(2,3-Dihydro)benzofuranyl]-5-hydroxy-1-(3,4-methylenedioxyphenyl)indane-2-carboxylic acid, m.p. 225–228° C.;

(1RS, 2SR, 3RS)-5-Hydroxy-3-(3,4-methylenedioxyphenyl)-1-(2,4,6-trimethoxyphenyl)indane-2-carboxylic acid, m.p. 225–226° C.;

(1RS, 2SR, 3SR)-1-[5-(2,3-Dihydro)benzofuranyl]-3-(4-methoxyphenyl)indane-2-carboxylic acid, m.p. 186–190° C.;

(1RS, 2SR, 3RS)-1-[3,4-(1,2-Ethylenedioxy)phenyl]-3-(4-methoxyphenyl)indane-2-carboxylic acid, m.p. 178–181° C.;

(1RS, 2SR, 3SR)-5-Hydroxy-3-(3,4-methylenedioxyphenyl)-1-(4-methoxyphenyl)indane-2-carboxylic acid, m.p. 124–127° C.;

(1RS, 2SR, 3RS)-5-Hydroxy-3-(4methoxyphenyl)-1-(2-methoxy-4,5-methylenedioxyphenyl)indane-2-carboxylic acid, m.p. 236–239° C.;

(1RS, 2S R, 3SR)-1-(3,4-Methylenedioxyphenyl)-3-(4-methoxyphenyl)-5-(propyl-1-yloxy)indane-2-carboxylic acid, m.p. 132–133° C.;

(1RS, 2SR, 3RS)-5-Methoxy-3-(4-methoxyphenyl)-1-(2-methoxy-4,5-methylenedioxyphenyl)indane-2-carboxylic acid, m.p. 149–150° C.;

(1RS, 2SR, 3RS)-3-[2-(2'-Carboxyphenoxy)-5-methoxyphenyl]-1-(3,4-methylenedioxyphenyl)-5-(prop-1-yloxy)indane-2 carboxylic acid, m.p. 245–247° C.;

(1RS, 2SR, 3RS)-3-[2-(2'-Carboxyphenoxy)-5-chloro-4-methoxyphenyl]-1-(3,4methylenedioxyphenyl)-5-(prop-1-yloxy)indane-2-carboxylic acid, m.p.. 199–201° C.;

(1RS, 2SR, 3RS)-3-[2-Carboxymethoxy-4-methoxyphenyl]-5-hydroxy-1-(3,4-methylenedioxyphenyl) indane-2-carboxylic acid, m.p. 182–185° C.

(1RS, 2SR, 3RS)-5-(But-1-yloxy)-3-(2-carboxymethoxy-4-methoxyphenyl)-1-(3,4methylenedioxyphenyl) indane-2-carboxylic acid, m.p. 211–212° C.

(1RS, 2SR, 3RS)-5-Butyl-3-(2-carboxymethoxy4methoxyphenyl)-1-(3,4-methylenedioxyphenyl)indane-2-carboxylic acid, m.p. 176–177° C.;

(1RS, 2SR, $^3$RS)-3-[2-(4'-Methoxyphenyl)-4-methoxyphenyl]-1-(3,4-methylenedioxyphenyl)-5-(prop-1-yloxy)indane-2-carboxylic acid, m.p. 147–148° C.;

(1RS, 2RS, 3RS)-1-(2-Carboxymethoxy-4methoxyphenyl]-3-(3,4-methylenedioxyphenyl)-4-(prop-1-yloxy)indane-2-carboxylic acid m.p. 201–206° C.;

(1RS, 2SR, 3SR)-3-[2-(3'-Aminopropyl)4methoxyphenyl]-1-(3,4-methylenedioxyphenyl)-5-(prop-1-yloxy)indane-2-carboxylic acid. (exact mass) M$^+$.: 503.2290 (Δ=+1.8 mDa for $C_{30}H_{33}O_6N$);

(1RS, 2SR, 3RS)-5-Metboxy-1-($^2$-methoxy-3,4-methylenedioxyphenyl)-3-(4-methoxyphenyl)indane-2-carboxylic acid m.p. 148–149° C.;

(1RS, 2SR, 3RS)-3-[2-(4'-Methoxy-2'-hydroxyphenyl)-4-methoxyphenyl]-1-(3,4-methylenedioxyphenyl)-5-1(prop-yloxy)indane-2-carboxylic acid, m.p. 199–200° C.;

(1RS, 2RS, 3RS)-3-(2-Carboxymethoxy-4-isopropyloxyphenyl)-1-(3,4-methylenedioxyphenyl)-5-(prop-1-yloxy)indane-2-carboxylic acid, m.p. 183–185° C.;

(1RS, 2SR, 3RS)-3-(2-Carboxymethoxy-4-ethyloxyphenyl)-1-(3,4-methylenedioxyphenyl)-5-(prop-1-yloxy)indane-2-carboxylic acid, m.p. 194–196° C.

(1RS, 2SR, 3RS)-3-(2-Carboxyethylmethoxy-4-methoxyphenyl)-1-(3,4-methylenedioxyphenyl)-5-(prop-1-yloxy)indane-2-carboxylic acid, m.p. 148–149° C.;

(1RS, 2SR, 3RS)-3-[2-[ ($^3$-Carboxypyridin-2-yloxy]-4-methoxyphenyl]-1-(3,4-methylenedioxyphenyl)-5-(prop-1-yloxy) indane-2 carboxylic acid m.p. 152–155° C.

(1RS, 2SR, 3RS)-3-[2-[Carbo(N,N-diethylcarbamoyl)methoxy]methoxy-4-methoxyphenyl]-1-(3,4-methylenedioxyphenyl)-5-(prop- 1-yloxy)indane-2-carboxylic acid, m.p. 181–182° C.;

(1RS, 2SR, 3RS)-1-(3,4-Methylenedioxyphenyl)-3,4-methoxy-2-(2-propen-1-yloxy)phenyl]-5-(prop-1-yloxy) indane-2-carboxylic acid, m.p. 168–170° C.;

(1RS, 3RS)-3-[2-(3'-Carboxyphenyl)4methoxyphenyl]-1-(3,4-methylenedioxyphenyl)-5-(prop-1-yloxy)indane dicyclohexylamine salt, m.p. 230–232° C.;

(1RS, 2SR, 3SR)-1,3,5-Tris(3,4-methylenedioxyphenyl)indane-2-carboxylic acid, Anal. Calc. for $C_{31}H_{22}O_8 \cdot \frac{5}{8}H_2O$: C, 69.76; H, 4.39. Found: C,69.81,H,4.46;

(1RS, 2SR, 3RS)-1-[2-(3-Hydroxyprop-1-yloxy)4,5-methylenedioxyphenyl]-3-(4methoxyphenyl)-5-(prop 1-yloxy)indane-2-carboxylate dicyclohexylamine salt, m.p. 165–167° C.;

(1RS, 2SR, 3RS)-1-(2-Methoxy-4,5-methylenedioxyphenyl)-3-(4-methoxyphenyl)-5-(prop-1-yloxy)indane-2-carboxylate dicyclohexylamine salt, m.p. 120–122° C.;

(1RS, 2SR, 3RS)-5-Methoxy-1-(4methoxy-2,3-methylenedioxyphenyl)-3-(4-methoxyphenyl)indane-2-carboxylate dicyclohexylamine salt, m.p. 187–188° C.;

(1RS, 2SR, 3RS)-5-(3-Buten- 1-yloxy)-3-(4methoxyphenyl)- 1-(3,4-methylenedioxyphenyl)indane-2-carboxylic acid, m.p. 127–129° C.;

(1RS, 2SR, 3RS)-5-(But-1-yloxy)-3-(4-methoxyphenyl)-1-(3,4-methylenedioxyphenyl)indane-2-carboxylic acid, m.p. 157–158° C.;

(1RS, 2RS, 3SR)-5-Hydroxy-1 (3,4-methylenedioxyphenyl)-3-(4-trifluoromethoxyphenyl)indane-2-carboxylic acid; m.p. 100–104° C.;

(1RS, 2SR, 3RS)-5-Hydroxy-1-(3-indolyl)-3-(4-methoxyphenyl)indane-2-carboxylic acid, m.p. 138–140° C.;

(1RS, 2SR, 3SR)-5-Hydroxy- 1-(5-indolyl)-3-(4methoxyphenyl)indane-2-carboxylate dicyclohexylamine salt, m.p. 235–240° C.;

(1RS, 2SR, 3SR)-3-(4-Methoxyphenyl)-1-(3,4methylenedioxyphenyl)-5-methylthioindane-2-carboxylic acid; Anal. Calc. for $C_{25}H_{22}O_5S \cdot \frac{1}{2}H_2O$: C, 67.70; H, 5.23. Found: C, 67.60; H, 5.40;

(1RS, 2RS, 3SR)-5,6-(Methylenedioxy)-1-(3,4-methylenedioxyphenyl)-3-(4-trifluoromethoxyphenyl)indane-2-carboxylic acid, m.p. 170–172° C.;

(1RS,2SR,3SR)-4-Benzyl-1,3-bis(4-methoxyphenyl)indane-2-carboxylate, dicyclohexylamine salt; m.p. 160–162° C.;

(1RS,2SR,3SR)-4-Benzyl-1-(4methoxyphenyl)-3-(3,4-methylenedioxyphenyl)indane-2carboxylic acid, dicyclohexylamine salt; m.p. 159–160° C.;

Trans, Trans-1,3-Bis(4-methoxyphenyl)indane-2-carboxamide, m.p. 223–225° C.;

(1RS,2SR,3SR)-5-Benzyloxy-1,3-bis(3,4-methylenedioxyphenyl)indane-2-carboxylic acid, m.p. 191–193° C.;

(1RS,2SR,3SR)-3-[4Methoxy-2-[2-(methylphosphinyl)eth-1-yl]phenyl]- 1-(3,4-methylenedioxyphenyl)-5-(prop-1-yloxy)indane-2-carboxylic acid disodium salt;

(exact mass) M$^+$+Na: 619.1462 (Δ=−1.2 mDa for $C_{30}H_{31}O_8PNa_3$)

(1RS,2SR,3RS, 1'RS, SR)-3-[2[-1'-carboxyeth-1'-yloxy)-4-methoxyphenyl]-1-(3,4-methylenedioxylphenyl)-5-(prop-1-yloxy) indane-2-carboxylic acid (1RS,2SR,3SR)-3-(4-Methoxyphenyl)- I-(3,4-methylenedioxyphenyl)-5-methylsulfoxylindane-2-carboxylic acid;

EXAMPLE 121

(1RS,2SR, 3RS)-3-[2-[(4-Carboxypyridin-3-yl)oxy]-4-methoxyphenyl]-1-(3,4-methylenedioxyphenyl)-5-(prop-1-yloxy)indane-2-carboxylate disodium salt:

a) Methyl (1RS,2SR, 3RS)-3-[2-[(4Formylpyridin-3-yl)oxy]-4-methoxyphenyl]-1-(3,4methylenedioxyphenyl)-5-(prop-1-yloxy) indane-2-carboxylate To a solution of Methyl (1RS, 2SR, 3RS)-3-(2-hydroxy-4-methoxyphenyl)-1-(3,4-methylenedioxyphenyl)-5-(prop-1-yloxy) indane-2-carboxylate (300 mg, 0.63 mmol) in DMF (4 mL) was added $K_2CO_3$ (109 mg, 0.79 mmol) and 3-fluoro-4 formylpyridine (150 mg, 1.2 mmol). The reaction mixture was heated to reflux under Argon for 2 h. After cooling to room temperature it was partitioned between 3N HCl and ethyl acetate. The ethyl acetate extract was washed with water, aqueous $NaHCO_3$ and brine and dried ($Mg_2SO_4$). The solvent was removed in vacuo. The residue was purified by flash column chromatography (silica gel, gradient elution from 10% to 20% ethyl acetate/hexanes) to afford the title compound (128 mg, 42%).

b) Methyl (1RS,2SR, 3RS)-3-[2-[(4Carboxypyridin-3-yl)oxy]-4-methoxyphenyl]-1-(3,4methylenedioxypbenyl)-5-(prop-1-yloxy) indane-2-carboxylate To a solution of Methyl (1RS, 2SR, 3RS)-3-[2-[(4-formylpyridin-3-yl)oxy]-4-methoxyphenyl]-1-(3,4-methylenedioxyphenyl)-5-(prop-1-yloxy) indane-2-carboxylate (128 mg, 0.24 mmol) in t-BuOH (10 mL) was added a solution of $NaClO_2$ (34 mg, 0.28 mmol) and $NH_2SO_3H$ (40 mg, 0.42 mmol) in water (6 mL). The reaction mixture was stirred at room temperature for 2 h and it was partitioned between water and ethyl acetate. The ethyl acetate extract was washed with water and brine and dried $(Mg_2SO_4)$. The solvent was removed in vacuo. The residue was purified by flash column chromatography (silica gel, 25% ethyl acetate/hexanes containing 5% of acetic acid) to afford the title compound (90 mg, 69%).

c) (1RS,2SR, 3RS)-3-[2-f(4-Carboxypyridin-3-yl)oxy]-4-methoxyphenyl-1-(3,4-methylenedioxyphenyl-5-(prop-1-yloxy) indane-2-carboxylic acid disodium salt To a solution of Methyl (1RS, 2SR, 3RS)-3-[2-[(4-Carboxypyridin-3-yl)oxy]-4-methoxyphenyl]-1-(3,4methylenedioxyphenyl)-5-(prop- 1-yloxy) indane-2-carboxylate (90, 0.15 mmol) in isopropanol (2 mL) was added 1M aqueous NaOH (0.3 mL, 0.3 mmol). The resulting mixture was heated to reflux for 12 h, then concentrated under reduced pressure. The residue was partitioned between dilute HCl and ethyl acetate. The ethyl acetate extract was washed with water and dried $(Mg_2SO_4)$. The solvent was removed in vacuo. The residue was purified by flash column chromatography (silica gel, 30% ethyl acetate/hexanes containing 5% of acetic acid) to afford the title compound (65 mg, 74%); m.p. 220–222° C. (dec.) (disodium salt).

EXAMPLE 122

2,2-Dimethylpropanoyloxymethyl (1RS,2SR,3RS)-3-(2-carboxymethoxy-4-methoxyphenyl)-1-(3,4methylenedioxyphenyl)-5-(prop-1-yloxy)-indane-2-carboxylate sodium salt a) 2,2-Dimethylpropanoyloxymethyl (1RS,2SR,3RS)-3-(2-hydroxy-4-methoxyphenyl)-1-(3,4methylenedioxyphenyl)-5-(prop-1-yloxy)-indane-2-carboxylate (1RS,2SR,3RS)-3-(2-hydroxy-4methoxyphenyl)-1-(3,4-methylenedioxyphenyl)-5-(prop-1-yloxy)-indane-2-carboxylic acid potassium salt (125 mg, 0.54 mmol) (obtained firm the treatment of the corresponding acid with $KHCO_3$ (54 mg, 0.54 mmol)) was dissolved in DMF (3 ml) and then pivaloyloxymethyl iodide (0.54 mmol) (prepared from pivaloyloxymethyl chloride (73 mg, 0.54 mmol) and excess sodium iodide in acetone) was added. The reaction mixture was stirred overnight and then partitioned between dil. HCl and ethyl acetate. The organic layer was washed with water and brine then dried.($MgSO_4$ anhyd.) filtered and evaporated. The product was purified by column chromatography to provide 122(a) (120 mg, 77%) as a colorless oil.

b) 2,2-Dimethylpropanoyloxymethyl (1RS, 2SR, 3RS)-3-(2-benzyloxycarbonylmethoxy-4-methoxyphenyl)-1-(3,4-methylenedioxyphenyl)-5-(prop-1-yloxy)indane-2-carboxylate.

2,2-Dimethylpropanoyloxymethyl (1RS,2SR,3RS)-3-(2-hydroxy-4-methoxyphenyl-1-(3,4-methylenedioxyphenyl)-5-prop-1-yloxy)-indane-2-carboxylate (280 mg, 0.5 mmol) in dry DMF (3 ml) was added to NaH (18 mg, 0.6 mmol) in a small volume of dry DMF. The mixture was stirred at RT for 20 min. then benzyl bromoacetate (137 mg, 0.6 mmol) was added. After stirring for 1.5 h the product was partitioned between 3M aqueous HCl and ethyl acetate. The organic layer was washed with water then brine, then dried ($MgSO_4$ anhyd.) filtered and evaporated to give an oil. The product was purified by column chromatography to provide 122 (b) (240 mg, 66%) as a colorless oil.

c) 2.2-Dimethylpropanoyloxymethyl (1RS,2SR,3RS)-3-(2-carboxymethoxy-4-methoxyphenyl)-1-(3,4-methylenedioxyphenyl)-5-(prop-1-yloxy-3-indane-2-carboxylic acid.

2,2-Dimethylpropanoyloxymethyl (1RS,2SR,3RS)-3-(2-benzyloxycarbonylmethoxy-4-methoxyphenyl)-1-(3,4-methylenedioxyphenyl)-5-(prop-1-yloxy)-indane-2-carboxylate (240 mg, 0.3 mmol) was dissolved in a 2:1 mixture of ethyl acetate and ethanol (3 ml) and then 50 mg of Pd/C was added. The mixture was stirred at room temperature under a $H_2$ atmosphere for 3 h. The catalyst was then filtered, the solvent concentrated in vacuo and the resultant oil purified by flash column chromatography. The title compound was obtained (180 mg, 86%) as a colorless oil.

MS (exact mass) $(M+Na)^+$.: 647.2335 (sodium salt)

(D=−2.3. mDa for $C_{33}H_{38}O_{11}Na$)

mp 190–195° C. (dec, sodium salt)

EXAMPLE 123

(1S, 2R, 3S)-3-[2-[Carbo-(1RS)- 1-(2-methoxy-2-methylpropionyloxy)eth-1-yloxymethoxyl]-4-methoxyphenyl-1-(3,4-methylenedioxyphenyl)-5-prop-1-yloxy)indane-2-carboxylate sodium salt a) Allyl (1S, 2R, 3S)-3-(4methoxy-2-methoxymethoxyphenyl)-1-(3,4-methylenedioxyphenyl)-5-(prop-1-yloxy)indane-2-carboxylate.

(1S, 2R, 3S)-3-(4-methoxy-2-methoxymethoxyphenyl)-1-(3,4-methylenedioxyphenyl)-5-(prop-1-yloxy)indane-2-carboxylic acid (4.8 g, 9.5 mmol) was dissolved in dry acetonitrile (30 MI) and DBU (1.7 ml, 11.4 mmol) was added followed by allyl bromide (3,4 g, 28. mmol). After stirring for 0.5 h. the product was partitioned between 3M aqueous HCl and ethyl acetate. The organic layer was washed with water and brine, then dried ($MgSO_4$ anhyd.) filtered and evaporated to give an oil. The product was purified by column chromatography to provide the title compound as a pale yellow oil (5.7 g, quantitative).

b) Allyl (1S, 2R, 3S)-3(2-hydroxy-4-methoxyphenyl)-1-(3,4-methylenedioxyphenyl)-5-(prop-1-yloxy)indane-2-carboxylate.

Allyl (1S, 2R, 3S)-3-(4-methoxy-2-methoxymethoxyphenyl)-1-(3,4-methylenedioxyphenyl)-(prop-1-yloxy)indane-2-carboxylate (1.7 g, 3.1 1 mmol) was dissolved in allyl alcohol (20 ml) and then 15 drops of conc. HCl was added. The resulting solution was stirred at 65° C. for 2 h. After removing the solvent the residue was partitioned between water and ethyl acetate. The organic layers were washed with water, 5% aqueous $NaHCO_3$ and brine; then dried ($MgSO_4$ anhyd.), filtered and evaporated to give an oil. The product was purified by column chromatography to provide the title compound as a pale yellow oil (1.26 g, 81%).

c) Allyl (1S, 2R, 3S)3-(2-Carbo-1-tert-butoxymethoxy-4-methoxyphenyl)-1-(3,4-methylenedioxyphenyl)-5-(prop-1-yloxy)indane-2-carboxylate.

Allyl (1S, 2R, 3S)-3-(2-Hydroxy-4-methoxyphenyl)-1-(3, 4-methylenedioxyphenyl)-5-(prop-1-yloxy)indane-2-carboxylate (1.0 g, 2 mmol) in dry DMF (4 ml) was added to NaH (57 mg, 2.4 mmol) in a small volume of dry DMF. The mixture was stirred at RT for 20 min., then tert-butyl bromoacetate (974 mg, 5 mmol) was added. After stirring for 0.5 h., the product was partitioned between 3M aqueous HCl and ethyl acetate. The organic layer was washed with water, brine and dried (MgSO$_4$ anhyd.), filtered and evaporated to give an oil. The product was purified by column chromatography to provide the title compound (1.1 g, 93%) as a pale yellow oil.

d) Allyl (1S, 2R, 3S)-3-(2-carboxymethoxy-4-methoxyphenyl)-1-(3,4-methylenedioxypbenyl)-5-(prop-1-yloxy)indane-2-carboxylate.

d) Allyl (1S, 2R, 3S)-3-(2-carbo-tert-butoxymethoxy-4-methoxyphenyl)-1-(3,4-methylenedioxyphenyl)-5-(prop-1-yloxy)indane-2-carboxylate (765 mg, 1.24 mmol) was dissolved in TFA (5 ml) containing a few drops of anisole. The reaction mixture was stirred at RT for 20 min. The solvent was eliminated, the residue was diluted with ethyl acetate, washed with water, brine and dried (MgSO$_4$ anhyd.), filtered and evaporated. The product was purified by column chromatography to provide the title compound (575 mg, 83%) as a colorless oil.

e) Allyl (1S, 2R, 3S)-3-[2-[Carbo(1RS)-1-(2-methoxy-2-methylpropionyloxy)eth-1-yloxymethoxy]-4-methoxphenyl-1-(3,4-methylenedioxyphenyl)-5-prop-1-yloxy)indane-2-carboxylic acid sodium salt Allyl (1S, 2R, 3S)-3-(2-carboxymethoxy-4-methoxyphenyl)-1-(3,4-methylenedioxyphenyl)-5-(prop-1-yloxy)indane-2-carboxylate (287 mg, 0.5 mmol) was dissolved in DMF (5 ml) and Cs$_2$CO$_3$ (333 mg, 1 mmol) added followed by (IS)-1-bromoethyl 2-methoxy-2-methylpropionate (225 mg, 1 mmol). The reaction mixture was stirred at RT overnight, then partitioned between water and ethyl acetate, washed with dil. HCl and brine, dried (MgSO$_4$ anhyd.), filtered and evaporated to give an oil. The product was purified by column chromatography to provide the title compound (260 mg, 74%) as a colorless oil.

f) (1S, 2R, 3S)-3-[2-[Carbo-(1RS)-1-(2-methoxy-2-metbylpropionyloxy)eth-1-yloxymethoxy]-4-methoxyphenyl]-1-3,4-methylenedioxyphenyl)-5-prop-1-yloxy)indane-2-carboxylic acid sodium salt Allyl (1S,2R,3S)-3-[2-Carbo(1RS)-1-(2-methoxy-2-methylpropionyloxyeth-1-yloxymethoxy]-4-methoxyphenyl]-1-(3,4-methylenedioxyphenyl)5-(prop-1-yloxy)indane-2-carboxylate (260 mg, 0.37 mmol) was dissolved in CH$_2$Cl$_2$ (2 ml) and tetrakis(triphenylphosphine)palladium(0) (36 mg, 0.037 mmol) added followed by tri-n-butyltin hydride (0.11 ml, 0.4 mol). The reaction mixture was stirred at RT for 3 h then quenched with 3N HCl and stirred for 20 min. The organic layer was diluted with ethyl acetate washed with water then brine, dried (MgSO$_4$ anhyd.), filtered and evaporated to give an oil. The product was purified by column chromatography to provide the title compound (210 mg, 85%) as a colorless oil.

MS (exact mass) (M+Na)$^+$.: 687.2415 (sodium salt)

(D=+0.3. mDa for C$_{36}$H$_{40}$O$_{12}$Na)

EXAMPLE 124

(1RS,2SR,3RS)-2-Amino-3-(2-carboxymethoxy-4-methoxyphenyl)-1-(3,4-methylenedioxyphenyl)-5-(prop-1-yloxy)-indane (1RS, 2SR, 3RS)-3-(2-tert--butoxycarbonylmethoxy-4-methoxyphenyl)-1-(3,4-methylenedioxyphenyl)5-(prop-1-yloxy)indane-2arboxylic acid (100 mg, 0.18 mmol), triphenylphosphonyl azide (0.03 ml, 0.18 mmol), and triethylamine (73 mg, 0.72 mmol) were dissolved in dry benzene (4 ml) and heated at 40° C. for 2 h and at 75° C. for 2 h. The reaction mixture was then partitioned between 1N HCl and ethyl acetate. The organic layer was washed with water and. brine, dried (MgSO$_4$ anhyd.), filtered and evaporated to give the corresponding isocianate as a colorless oil. After purification by column chromatography (silica gel, ethyl acetate/hexane 30:70), the isocianate (100 mg) thus obtained was dissolved in IM HCl in dioxane (3 mL) and the mixture was heated at 80° C. overnight. The solvent was removed in vacuo, the residue was partitioned between ethyl acetate and water. The organic layer was washed with brine, dried (MgSO$_4$) and concentrated to give a colorless oil that was purified by HPLC (1:1 CNCH$_3$:H$_2$O (containing 0.1% TFA)) to produce the desired product (40 mg, 42%) as an off-white solid, m.p. 181–182° C. (dec).

EXAMPLE 125

(1RS,2SR,3RS)-2-Aminomethyl-3-(2-carboxymethoxy-4-methoxyphenyl)-1-(3,4-methylenedioxyphenyl)-5-(prop-1-yloxy)-indane a) (1RS, 2SR, 3RS)-2-Hydroxymethyl-3-(2-tert-butoxycarbonylmethoxy-4-methoxyphenyl)-1-(3,4-methylenedioxyphenyl)-5-(prop-1-yloxy)indane (1RS, 2SR, 3RS)-2-Hydroxymethyl-3-(2-hydroxy-4-methoxyphenyl)-1-(3,4-methylenedioxyphenyl)-5-(prop-1-yloxy)indane (634 mg, 1.43 mmol) was dissolved in dry acetone (15 ml) then K$_2$CO$_3$ (1.97 g, 14.3 mmol) and tert-butyl bromoacetate (416 mg, 2.14 mmol) was added. The reaction mixture was stirred overnight. The solvent was then eliminated theresidue partitioned between water and ethyl acetate. The organic layer was washed with dilute HCl, water, brine and dried (MgSO$_4$ anhyd.) filtered and evaporated to give an oil. The product was purified by column chromatography to provide 125(a) (792 g, 98%) as a pale yellow oil.

b) (1RS, 2SR, 3RS)-2-Azidomethyl-3-(2-tert-butoxycarbonylmethoxy-4-methoxyphenyl)-1-(3,4-methylenedioxyphenyl)-5-(prop-1-yloxy)indane (1RS, 2SR, 3RS)-2-Hydroxymethyl-3-(2-2-tert-butoxycarbonylmethoxy-4-methoxyphenyl)-1-(3,4-methylenedioxyphenyl)-5-(prop-1-yloxy)indane (792 mg, 1.41 mmol) was dissolved in CH$_2$Cl$_2$ (10 ml) cooled at 0° C., triethylamine (485 mg, 4.8 mmol) and methanesulfonyl chloride (229 mg, 2 mmol) were then added. The reaction mixture was kept at 0° C. for 0.5 h and then partitioned between water and ethyl acetate. The organic layer was washed with dilute HCl, water, brine and dried (MgSO$_4$ anhyd.) filtered and evaporated to produce the desired mesylate (680 mg, 78%). Without further purification, the mesylate was dissolved in dry DMF (5 ml), and NaN$_3$ was added. The reaction mixture was stirred overnight at 60° C. and, after cooling to RT, it was partitioned between water and ethyl acetate. The organic layer was washed with dilute HCl, water, brine and dried (MgSO$_4$ anhyd.) filtered and evaporated. The residue was purified by column chromatography to produce the desired azide as a colorless oil (484 mg, 75%).

c) 1RS, 2SR, 3RS)-2-Aminomethyl-3-(2-tert-butoxycarbonylmethoxy-4-methoxyphenyl)-1-(3,4-methylenedioxyphenyl)-5-(prop-1-yloxy)indane (1RS, 2SR, 3RS)-2-Azidomethyl-3-(2-2-tert-butoxycarbonylmethoxy-4-methoxyphenyl)-1-(3,4-methylenedioxyphenyl)-5-(prop-1-yloxy)indane (484 mg, 0.78 mmol) was dissolved in ethanol (12 ml) and ethyl acetate (3 ml) and then 80 mg of 10% Pd/C were added. The reaction mixture was stirred under H$_2$ atmosphere for 4 h. The catalyst was filtered, the solvent eliminated and the residue purified by column chromatography (ethyl acetate/hexane 25/75 followed by methanol) to obtained the desired amine (320 mg, 66%) as a colorless oil.

d) (1RS, 2SR, 3RS)-2-Aminomethyl-3-(2-carboxymethoxy-4-methoxyphenyl)-1-(3,4methylenedioxyphenyl)-5-(prop-1-yloxy)indane (1RS, 2SR, 3RS)-2-Aminomethyl-3-(2-2-tert-butoxycarbonylmethoxy)-1-methoxyphenyl)-1-(3,4-methylenedioxyphenyl)-5-(prop-1-yloxy)indane (765 mg, 1.24 mmol) was dissolved in TFA (5 ml) containing a few drops of anisole. The reaction mixture was stirred at RT for 20 min. The solvent was eliminated the residue was diluted with ethyl acetate washed with water, brine and dried (MgSO$_4$ anhyd.), filtered and evaporated. The product was purified by column chromatography to provide the tide compound (575 mg, 83%) as a white powder m.p. 237–242° C.

EXAMPLES 126–153

Indan-5-yl-(1RS,2SR,3RS)-3-(2carboxymethoxy-4-methoxyphenyl)-1-(3,4-methylenedioxyphenyl)-5-prop-1-yloxy)-indane-2-carboxylic acid sodium salt. m.p. 181–183° C. dec.

3,5-Dimethoxyphenyl-(1RS,2SR,3RS)-3-(2-carboxymethoxy-4-methoxyphenyl-3-1-(3,4methylenedioxyphenyl)-5-(prop-1-yloxy)-indane-2-carboxylate acid sodium salt m.p. 185–189° C. dec.

(1RS)-1-(2-Methoxy-2-methylpropionyloxy)eth-1-yl (1RS,2SR,3RS)-3-(2-carboxymethoxy-4-methoxyphenyl) 1-(3-methylenedioxyphenyl)-5-(prop-1-yloxy)indane-2-carboxylate sodium salt m.p. 178–181° C. dec.

N,N-Dimethylcarbamoylmethyl (1RS,2SR,3RS)-3-(2-carboxymethoxy-4-methoxyphenyl)-1-(3,4-methylenedioxyphenyl)-5-(prop-1-yloxy)indane-2-carboxylate sodium salt m.p. 170–174° C. dec.

Ethoxycarboxyloxymethyl (1RS,2SR,3RS)-3-(2-carboxymethoxy-4-methoxphenyl)-1-(3,4-methylenedioxyphenyl)-5-(prop-1-yloxy)indane-2-carboxylate sodium salt MS (exact mass) (M+Na)$^+$: 645.1959 (sodium salt)

(D=−1.1 mDa for C$_{33}$H$_{34}$O$_{12}$Na)

Benzoyloxymethyl (1RS,2SR,3RS)-3-(2-carboxymethoxy-4-methoxyphenyl)-1-(3,4-methylenedioxyphenyl)-5-(prop-1-yloxy)indane-2-carboxylate sodium salt MS m/e 672(M+NH$_4$)$^+$ Cyclohexyloxycarboxyloxymethyl (1RS,2SR,3RS)-3-(2-carboxymethoxy-4-methoxyphenyl)-1-(3,4-methylenedioxyphenyl)-5-(prop-1-yloxy)indane-2-carboxylate sodium salt MS (exact mass) (M+Na)$^+$: 699.2453 (sodium salt)

(D=−3.5. mDa for C$_{37}$H$_{40}$O$_{12}$Na)

Ethyl (1RS,2SR,3RS)-3-(2-carboxymethoxy-4-methoxyphenyl)-1-(3,4-methylenedioxyphenyl)-5-(prop-1-yloxy)indane-2-carboxylate sodium salt MS (exact mass) M$^+$: 548.2040 (free acid)

(D=+0.6. mDa for C$_{31}$H$_{32}$O$_9$)

(1S,2R,3S)-3-[[(2-Carboxy-(2',6'-dimethylphenyl)methoxy]-4-methoxybenyl]-1-(3,4-methylenedioxyphenyl)-5-(prop-1-yloxy)indane-2-carboxylate sodium salt MS (exact mass) (M+Na)$^+$,: 647.2264 (sodium salt)

D=−0.7. mDa for C$_{37}$H$_{36}$O$_9$Na)

(1S,2R,3S)-3-[[(2-Carboxycyclopentylmethoxy)-4-methoxyphenyl]-1-(3,4-methylenedioxyphenyl)-5-(prop--yloxy)indane-2-carboxylate sodium salt MS (exact mass) (M+Na)$^+$: 611.2282 (sodium salt)

(D=−2.5. mDa for C$_{34}$H$_{36}$O$_9$Na)

(1S,2R,3S)-3-[2-[Carbo(indan-5-yloxy)methoxy]-4-methoxyphenyl]-1-(3,4-methylenedioxyphenyl)-5-(prop-1-yloxy)indane-2-carboxylic acid sodium salt MS (exact mass) (M+Na)$^+$: 659.2281 (sodium salt)

(D=−2.4. mDa for C$_{38}$H$_{36}$O$_9$Na)

(1S,2R,3S)-3-[2-Carbo(eth-1-yloxy)methoxy]-4-methoxyphenyl]-1-(3,4-methylenedioxyphenyl)-5-prop-1-yloxy)indane-2-carboxylic acid sodium salt MS (exact mass) (M+2Na—H)$^+$: 593.1769 (sodium salt)

(D=−0.6 mDa for C$_{31}$H$_{31}$O$_9$Na$_2$)

(1RS,2SR,3RS)-3-(2-Carboxyethylmethoxy-4-methoxyphenyl)-1-(3,4-methylenedioxyphenyl)-5-prop-1-yloxy )indane-2-carboxylic acid m.p. 148–149° C.

(1RS,2SR,3RS)-3-[2-[2-[2-(Diethylamino)-2-oxoethoxy]-2-oxoethoxyl-4-methoxyphenyl)-1-(3,4-methylenedioxyphenyl)-5-(prop-1-yloxy)indane-2-carboxylic acid m.p. 181–182° C.

(1RS,2SR, 3RS)-2-Trifluoromethylsulfonamidomethyl-3-(2-carboxymethoxy-4-methoxyphenyl)-1-(3,4-methylenedioxyphenyl)-5-(prop-1-yloxy)indane m.p. 184–186° C.

(1RS,2SR,3RS)-2-Aminoethyl-3-(2-carboxymethoxy-4-methoxyphenyl)-1-(3,4-methylenedioxyphenyl)-5-(prop-1-yloxy)indane m.p. 207–211° C.

Indan-5-yl (1S,2R,3S)-3-(2-carboxymethoxy-4-methoxyphenyl)-1-(3,4-methylenedioxyphenyl)-5-(prop-1-yloxy)indane-2-carboxylate sodium salt Cyclopentyl (1S,2R,3S)-3-(2-carboxymethoxy-4-methoxyphenyl)-1-(3,4-methylenedioxyphenyl)-5-(prop-1-yloxy)indane-2-carboxylate sodium salt.

Ethoxycarboxymethyl (1S,2R,3S)-3-(2-carboxymethoxy-4-methoxyphenyl-1-(3,4-methylenedioxyphenyl-3-5-(prop-1-yloxy)indane-2-carboxylate sodium salt.

(1RS)-1-(1-Methylethoxycarboxy)eth-1-yl (1RS,2SR, 3RS)-3-(2-carboxymethoxy-4-methoxyphenyl)-1-(3,4-methylenedioxyphenyl)-5-(prop-1-yloxy)indane-2-carboxylate sodium salt.

m.p. 151–155° C.

Ethyl (1S,2R,3S)-3-(2-carboxymethoxy-4-methoxyphenyl)-1-(3,4-methylenedioxyphenyl-5-(prop-1-yloxy)indane-2-carboxylate sodium salt (1S,2R,3S)-3-[2-Carbomethoxymethoxy-4-methoxyphenyl]-1-(3-methylenedioxyphenyl)-5-[prop-1-yloxy)indane-2-carboxylic acid sodium salt (1S,2R,3S)-3-[2-[Carbobenzoyloxymethoxymethoxy-4-methoxyphenyl]-1-(3,4-methylenedioxyphenyl)-5-(prop-1-yloxy)indane-2-carboxylic acid sodium (1 S.2R.3S)-3-[2-(Carboethoxycarboxyloxymethoxymethoxy)-4-methoxyphenyl]-1- (3,4-methylenedioxyphenyl)-5-(prop-1-yloxy)indane-2-carboxylic acid sodium salt (1S,2R,3S)-3-[2-(Carboacetoxymethoxymethoxymethoxyphenyl]-1-(3,4-methylenedioxyphenyl)-5-(prop-1yloxy)indane-2-carboxylic acid sodium salt (1S,2R,3S)-3-[2-[Carbophthalidylmethoxy)-4-methoxyphenyl]-1-(3,4-methylenedioxyphenyl)-5-(prop-1-yloxy)indane-2-carboxylic acid sodium salt (1S,2R,3S)-3-2-Carbo-(2-metboxy-2-methylpropionyloxymethoxymethoxy]-4-methoxyphenyl]-1-(3,4-methylenedioxypbenyl)-5-(prop-1-yloxy)indane-2-carboxylic acid sodium salt

EXAMPLE 153

(1S,2R,3S)-3-[2-Carbo-(2,2-dimethylpropanoyloxymethoxymethoxy]-4-methoxyphenyl]-1-(3,4-methylenedioxyphenyl)-5-(prop-1-yloxy)indane-2-carboxylic acid sodium salt To a solution of (1S,2R,3S)-3-[2-Carboxymethoxy-4methoxyphenyl]-1-(3,4-methylenedioxyphenyl)-5-(prop-1-yloxy)indane-2-carboxylic acid monopotassium salt (170 mg, 0.3 mmol) (obtained by treatment of the corresponding diacid (156 mg, 0.3 mmol) with I equiv. of $KHCO_3$ (30 mg, 0.3 mmol)) in DMF (4 mL) pivaloyloxymethyl iodide (74 mg, 0.3 mmol) was added. The reaction mixture was stirred at RT for 0.5 h and more pivaloyloxymethyl iodide was then added (20 mg. 0.08 mmol) and then stirred for an additional 0.5 h. The reaction mixture was partitioned between dilute aqueous HCl and ethyl acetate. The ethyl acetate extract was washed with water and brine and dried ($MgSO_4$ anhydrous). The solvent was removed in vacuo and the residue was purified by flash column chromatography (silica gel, Ethyl Acetate/hexane/HOAc 30/65/5) to obtain the desired compound as a white foam (140 mg, 73%) as the free acid which was converted to its sodium salt. m.p. 128–133° C.

MS (exact mass) $M^++Na$: 679.2116 (sodium salt)

(D=+1.2 mDa for $C_{35}H_{37}O_{11}Na_2$)

EXAMPLE 154

(1RS,2SR, 3RS)-3-(2-Carboxymethoxy-4-methoxyphenyl)-1-(3,4-methylenedioxyphenyl)-5-(prop-1-yloxy)indan-2-ylacetic acid a) (1RS,2SR, 3RS)-3-(4-Methoxy-2-methoxymethoxyphenyl)-1-(3,4-methylenedioxyphenyl)-5-(prop-1-yloxy)indane-2-carboxylic acid. A solution of methyl (1RS, 2RS, 3RS)-3-(4methoxy-2-methoxymethoxyphenyl)-1-(3,4-methylenedioxyphenyl)-5-(prop-1-yloxy)indane-2-carboxylate (2.42 g, 4.6 mmol) in isopropyl alcohol (30 ml) with aqueous NaOH (8 ml of 5 N solution) was refluxed for 4 h. The resultant mixture was partitioned between EtOAc and 3N HCl. The organic extract was washed with $H_2O$ then brine, dried ($Na_2SO_4$) and solvent removed in vacuo to afford the title compound as a colorless oil (1.98 g, 84%).

b) Methyl (1RS,2SR, 3RS)-3-(4-methoxy-2-methoxymethoxyphenyl)-1-(3,4-methylenedioxyphenyl)-5-(prop-1-yloxy)indane-2-carboxylate. To a solution of(1RS, 2SR, 3RS)-3-(4-methoxy-2-methoxymethoxyphenyl)-1-(3, 4-methylenedioxyphenyl)-5-(prop-1-yloxy)indane-2-carboxylic acid (1.98 g, 3.91 mmol) in acetonitrile (15 ml) was added DBU (0.655 g, 4.3 mmol) followed by iodomethane (2.77 g, 19.5 mmol). The reaction mixture was stirred at room temperature 3.5 h then partitioned between EtOAc and 3N HCl. The organic extract was washed with $H_2O$, saturated $NaHCO_3$ solution, $H_2O$, then brine, dried ($Na_2SO_4$) and solvent removed in vacuo to provide the title compound (1.79 g, 88%) as an oil.

c) (1RS,2RS,3RS)-2-Hydroxymethyl-3-(4-methoxy-2-methoxymethoxyphenyl)-1-(3,4-methylenedioxyphenyl)-5-(prop-1-yloxy)indane.

To a solution of methyl (1RS, 2SR, 3RS)-3-(4-methoxy-2-methoxymethoxyphenyl)-1-(3,4-methylenedioxyphenyl)-5-(prop-1-yloxy)indane-2-carboxylate (4.45 g, 8.5 mmol) in THF (35 ml) stirred at 0° C. was added lithium aluminum hydride (17 ml of a 1 M solution in THF). The cooling bath was removed and stirring continued for 18 h. The reaction was quenched by addition of saturated aqueous ammonium chloride solution then partitioned between EtOAc and 3N HCl. The organic extract was washed with $H_2O$, saturated $NaHCO_3$ solution, $H_2O$, then brine, dried ($Na_2SO_4$) and solvent removed in vacuo to afford the title compound as an oil (4.13 g, 98%).

d) (1RS,2RS,3RS)-2-Methanesulfonyloxymethyl-3-(4-methoxy-2-methoxymethoxyphenyl)-1-(3,4-methylenedioxyphenyl)-5-(prop-1-yloxy)indane.

To a solution of (1RS, 2RS, 3RS)-2-hydroxymethyl-3-(4-methoxy-2-methoxymethoxyphenyl)-1-(3,4-methylenedioxyphenyl)-5-(prop-1-yloxy)indane (1.388 g, 2.82 mmol) in methylene chloride (10 ml) with TEA (1.2 ml) stirred under argon at 0° C was added methanesulfonyl chloride (0.41 g, 3.5 mmol). The cooling bath was removed and stirring continued for 1 h. The mixture was partitioned between EtOAc and 3N HCl. The organic extract was washed with $H_2O$, saturated $NaHCO_3$ solution, $H_2O$, then brine, dried ($Na_2SO_4$) and solvent removed in vacuo to afford the title compound as an oil (1.52 g, 95%).

e) 1RS,2RS,3RS)-2-Cyanomethyl-3-(4-methoxy-2-methoxymethoxyphenyl)-1-(3,4-methylenedioxyphenyl)-5-(pro I -yloxy)indane. (1RS,2RS,3RS)-2-Methanesulfonyloxymethyl-3-(4-methoxy-2-methoxymethoxyphenyl)-1-(3,4-methylenedioxyphenyl)-5-(prop-1-yloxy)indane (1.5 g, 2.96 mmol) was stirred in DMF (10 ml) under argon with NaCN (1.45 g, 29.6 mmol) at 60° C. for 20 h then cooled and partitioned between EtOAc and 3N HCl. The organic extract was washed with $H_2O$, saturated $NaHCO_3$ solution, $H_2O$, then brine, dried ($Na_2SO_4$) and solvent removed in vacuo to afford the title compound as an oil (1.27 g, 86%).

f) 1RS,2RS,3RS)-2-Cyanomethyl-3-(2-hydroxy-4-methoxyphenyl)- 1-(3,4-methylenedioxyphenyl)-5-(prop-1-yloxy)indane. 1RS,2RS,3RS)-2-Cyanomethyl-3-(4-methoxy-2-methoxymethoxyphenyl)-1-(3,4-methylenedioxyphenyl)-5-(prop-1-yloxy)indane (300 mg, 0.60 mmol) was dissolved in EtOH (4 ml) with concentrated HCl (0.1 ml) then refluxed for 1 h. the mixture was cooled then partitioned between EtOAc and 3N HCl. The organic extract was washed with $H_2O$, saturated $NaHCO_3$ solution, $H_2O$, then brine, dried ($Na_2SO_4$) and solvent removed in vacuo to afford the title compound as a solid foam (250 mg, 91%).

g) 1RS,2RS,3RS)-3-(2-Carbo-t-butoxymethoxy-4-methoxyphenyl)-2-cyanomethyl-1-(3, 4methylenedioxyphenyl)-5-(prop-1-yloxy)indane. To a solution of 1RS,2RS,3RS)-2-cyanomethyl-3-(2-hydroxy-4-methoxyphenyl)-1-(3,4-methylenedioxyphenyl)-5-(prop-1-yloxy)indane (250 mg, 0.55 mmol) in DMF (4 ml) stirred at 0° C. under argon added NaH (21 mg of 80% oil dispersion, 0.7 mmol). The mixture stirred at 0° C. for 15 min then t -butylbromoacetate (107 mg, 0.55 mmol) was added. The cooling bath was removed and the mixture was stirred for 3 h at room temperature then partitioned between EtOAc and 3N HCl. The organic extract was washed with $H_2O$, saturated $NaHCO_3$ solution, $H_2O$, then brine, dried ($Na_2SO_4$) and solvent removed in vacuo. The residue was purified by flash chromatography on silica gel, (eluent 25–50% $Et_2O$/hexanes) to afford the title compound as an oil (247 mg, 79%).

h) 1RS,2RS,3RS)-3-(2-Carboxymethoxy-4-methoxyphenyl)-2-cyanomethyl-1-(3,4-methylenedioxyphenyl-5-(prop-1-yloxy)indane. 1RS,2RS,3RS)-3-(2-Carbo-t-butoxymethoxy-4-methoxyphenyl)-2-cyanomethyl-1-(3,4-methylenedioxyphenyl)-5-propoxyindane (240 mg, 0.42 mmol) was stirred in methylene chloride (3 ml) with TFA (0.8 ml) under argon at room temperature for 1 h then partitioned between EtOAc and 3N HCl. The organic extract was washed with $H_2O$ then brine, dried (Na2SO4) and solvent removed in vacuo to afford the product as an oil (190 mg, 88%).

i) (1RS,2SR,3RS)-3-(2-Carboxymethoxy-methoxyphenyl)-1-(3,4-methylenedioxyphenyl)-5-(prop-1-yloxy)indan-2-ylacetic acid. To a solution of 1RS,2RS,3RS)-3-(2-carboxymethoxy-4-methoxyphenyl)-2-cyanomethyl-1-(3,4-methylenedioxyphenyl)-5-prop-1-yloxy)indane (290 mg, 0.56 mmol) in methanol (ca. 1 ml) was added aqueous 2 N NaOH solution (0.3 ml) followed by $H_2O$ (8 ml) then (with caution) $Na_2O_2$ (120 mg). The mixture was heated to 70° C. and stirred for 20 h at which time HPLC showed only 15% hydrolysis. The mixture was stirred at 85° C. for 3 days with 3 (100 mg) portions of $Na_{22}$ added each day. the reaction mixture was partitioned between EtOAc and 3N HCl. The organic extract was washed with $H_2O$ then brine, dried ($Na_2SO_4$) and solvent removed in vacuo to afford the product as an oil (228 mg, 90% pure by HPLC) Final purification was obtained by crystallization as the bis cyclohexylamine salt. mp 210–212° C.

EXAMPLE 155

Following the procedure outlined on Example 154 the following compound was made: (1RS,2SR,3RS)-3-(2-carboxymethoxy-4-methoxyphenyl)-1-(3,4-methylenedioxyphenyl)-5-(prop-1-yloxy)indane-2-yl-acetic acid. m.p. 139–146°

EXAMPLE 156

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

What is claimed is:

1. A compound selected from the group consisting of:

Methyl-3-(3,4-Methylenedioxypbenyl)-6-(prop-1-yloxy)-1-oxo-indene-2-carboxylate;

Methyl-( 1RS)- 1-hydroxy-(4-methoxy-2-methoxymethoxyphenyl)- 1-3-(3,4-methylenedioxyphenyl)-6-(prop-1-yloxy)indene-2-carboxylate;

(+)Methyl-(1S,2S,3S)-3-(4-methoxy-2-methoxymethoxyphenyl)-1-(3,4-methylenedioxyphenyl)-5-(prop-1-yloxy)indane-2-carboxylate;

(+)Methyl-(1S,2S,3S)-3-(2-Hydroxy-4-methoxyphenyl)-1-(3,4-methylenedioxyphenyl)-5-(prop-1-yloxy)indane-2-carboxylate;

(+)Methyl-(1S,2S,3S)-3-(2-Carboethoxymethoxy-4-methoxyphenyl)-1-(3,4-methylenedioxyphenyl)-5-(prop-1-yloxy)indane-2-carboxylate; or Methyl (1SR, 2SR, 3SR)-3-[2-(2-hydroxyeth-1-yloxy)methoxyphenyl]-1-(3,4-methylenedioxy phenyl)-5-propoxyindane-2-carboxylate.

2. A compound of claim 1 which is Methyl-3-(3,4-Methylenedioxyphenyl)-6-(prop-1-yloxy)- 1-oxo-indene-2-carboxylate.

3. A compound of claim 1 which is Methyl-(1RS)-1-hydroxy-(4-methoxy-2-methoxymethoxyphenyl)-1-3-(3,4-methylenedioxyphenyl)-6-(prop-1-yloxy)indene-2-carboxylate.

4. A compound of claim 1 which is (+)Methyl-(1S,2S,3S)-3-(4-methoxy-2-methoxymethoxyphenyl)-1-(3,4-methylenedioxyphenyl)-5-(prop-1-yloxy)indane-2-carboxylate.

5. A compound of claim 1 which is (+)Methyl-(1S,2S,3S)-3-(2-Hydroxy-4-methoxyphenyl)-1-(3,4-methylenedioxyphenyl)-5-(prop-1-yloxy)indane-2-carboxylate.

6. A compound of claim 1 which is (+)Methyl-(1S,2S,3S)-3-(2-Carboethoxymethoxy-4-methoxyphenyl)-1-(3,4-methylenedioxyphenyl)-5-(prop-yloxy)indane-2-carboxylate.

7. A compound of claim 1 which is Methyl (1SR, 2SR, 3SR)-3-[2-(2-hydroxyeth-1-yloxy)-4-methoxyphenyl]-1-(3,4-methylenedioxy phenyl)-5-propoxyindane-2-carboxylate.

* * * * *